(12) United States Patent
Fortuna et al.

(10) Patent No.: US 10,925,560 B2
(45) Date of Patent: Feb. 23, 2021

(54) IMAGING DEVICE

(71) Applicant: Imaginalis S.R.L., Florence (IT)

(72) Inventors: Damiano Fortuna, Florence (IT);
Leonardo Manetti, Arezzo (IT);
Massimiliano Leonori, Lucca (IT);
Tommaso Pavanello, Pisa (IT); Giulio Raimondi, Pisa (IT); Riccardo Apreda, Pisa (IT)

( * ) Notice: Subject to any disclaimer, the term of this patent is extended or adjusted under 35 U.S.C. 154(b) by 416 days.

(21) Appl. No.: 15/771,374

(22) PCT Filed: Oct. 27, 2016

(86) PCT No.: PCT/IB2016/056461
§ 371 (c)(1),
(2) Date: Apr. 26, 2018

(87) PCT Pub. No.: WO2017/072686
PCT Pub. Date: May 4, 2017

(65) Prior Publication Data
US 2020/0146642 A1    May 14, 2020

(30) Foreign Application Priority Data

Oct. 29, 2015 (IT) .......................... UB2015A004931
Oct. 29, 2015 (IT) .......................... UB2015A005187

(51) Int. Cl.
*A61B 6/00* (2006.01)
*A61B 6/03* (2006.01)

(52) U.S. Cl.
CPC ............ *A61B 6/4405* (2013.01); *A61B 6/035* (2013.01); *A61B 6/037* (2013.01); *A61B 6/4447* (2013.01); *A61B 6/487* (2013.01)

(58) Field of Classification Search
CPC .............................. A61B 6/035; A61B 6/4405
See application file for complete search history.

(56) References Cited

U.S. PATENT DOCUMENTS

2003/0072416 A1    4/2003  Rasche et al.
2015/0208990 A1*   7/2015  Stoutenburgh ....... A61B 6/0442
                                                          378/62

FOREIGN PATENT DOCUMENTS

JP    H02228946 A1    9/1990
WO    2003070101 A1    8/2003
WO    2014001834 A1    1/2014

OTHER PUBLICATIONS

PCT International Search Report dated Mar. 7, 2017 in corresponding PCT Application No. PCT/IB2016/056461 filed Oct. 27, 2016, inventor Fortuna, Damiano et al.

* cited by examiner

*Primary Examiner* — Dani Fox
(74) *Attorney, Agent, or Firm* — Steptoe & Johnson LLP; Robert Greenfeld

(57) ABSTRACT

An imaging device including a gantry defining an analysis zone and a circular trajectory of extension extending around a central axis. The gantry includes an acquisition unit having at least a detector suitable to receive said radiation after said radiation has passed through the analysis zone, and a casing defining a housing volume for the detector and including a curved base module and a curved mobile module movable relative to the curved base module so as to vary the angular extension of the casing. A carriage is housed in the housing volume to which the image acquisition unit is attached. There is a base guideway integral with the curved base module defining a base sliding trajectory for the carriage in the curved base module, and a mobile guideway integral with and inside the curved mobile module and defining a mobile sliding trajectory for the carriage in the curved mobile module.

13 Claims, 14 Drawing Sheets

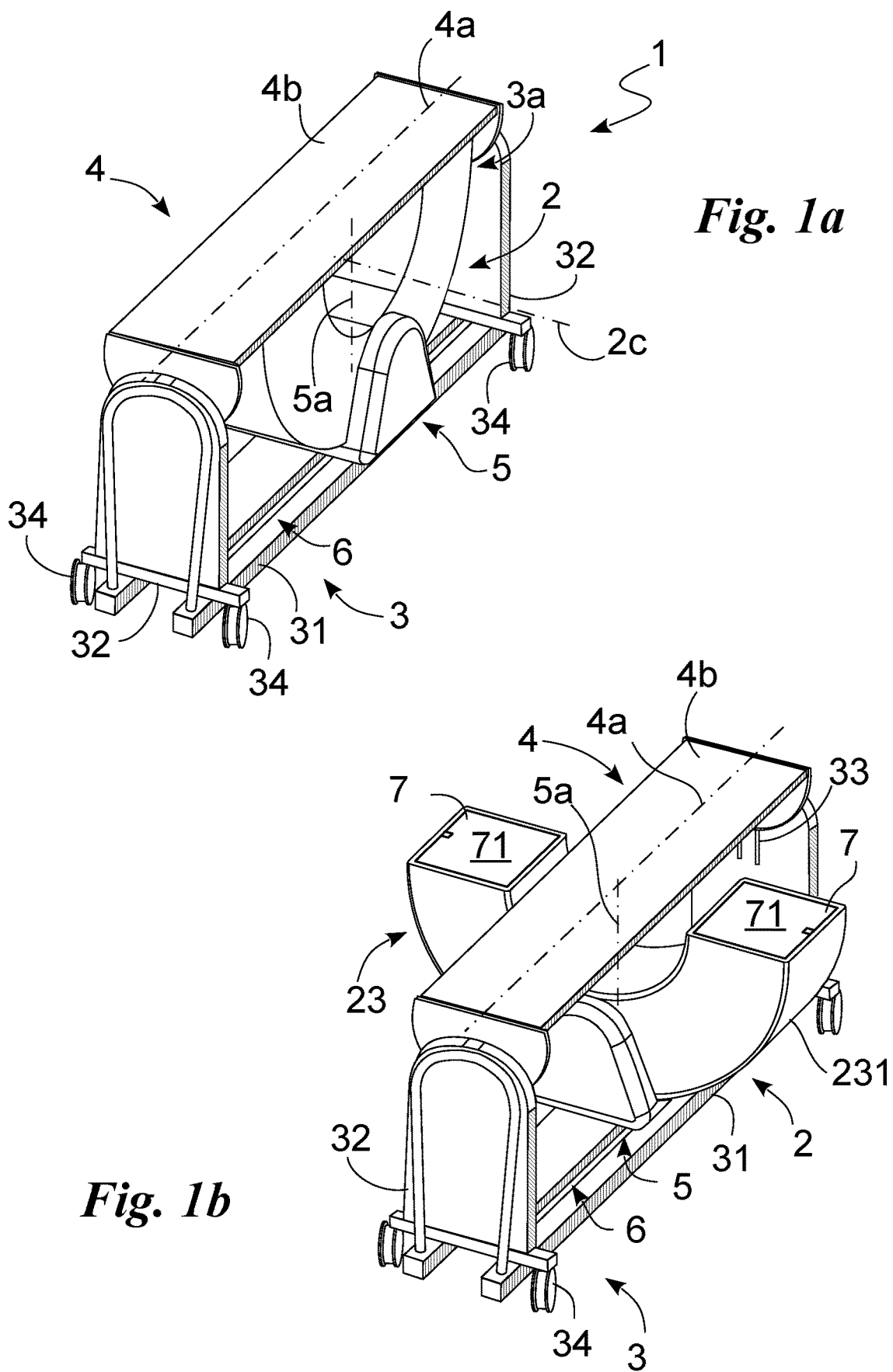

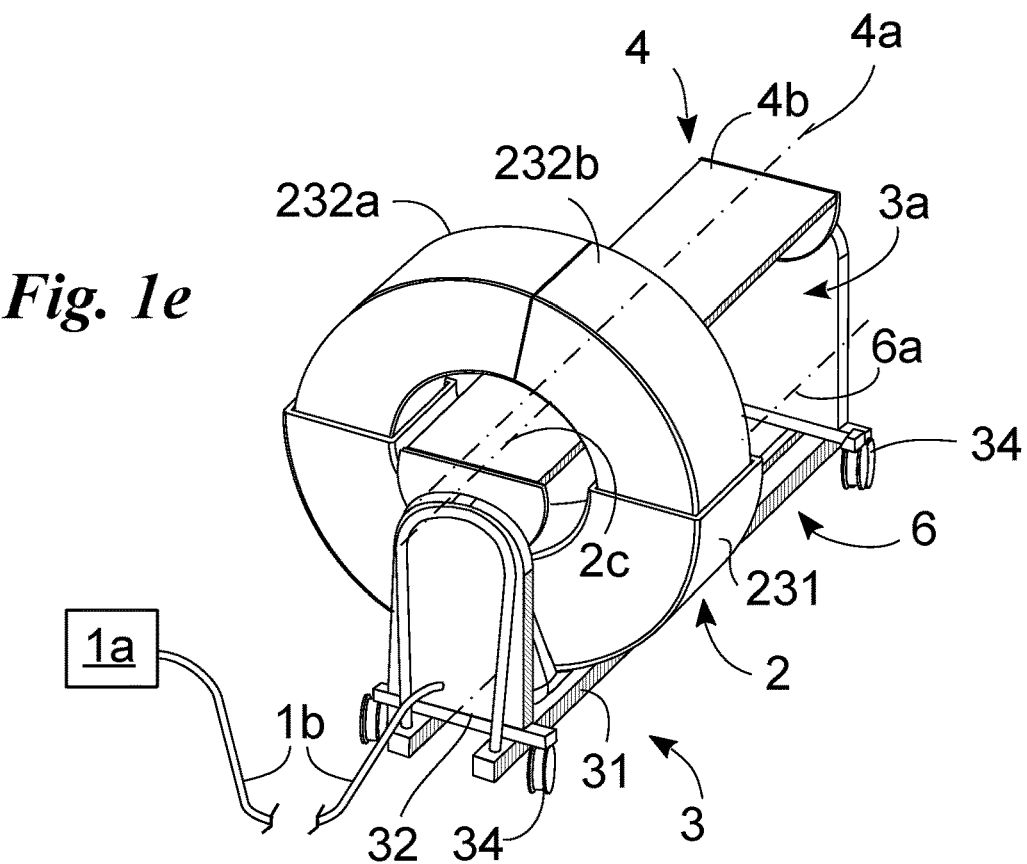

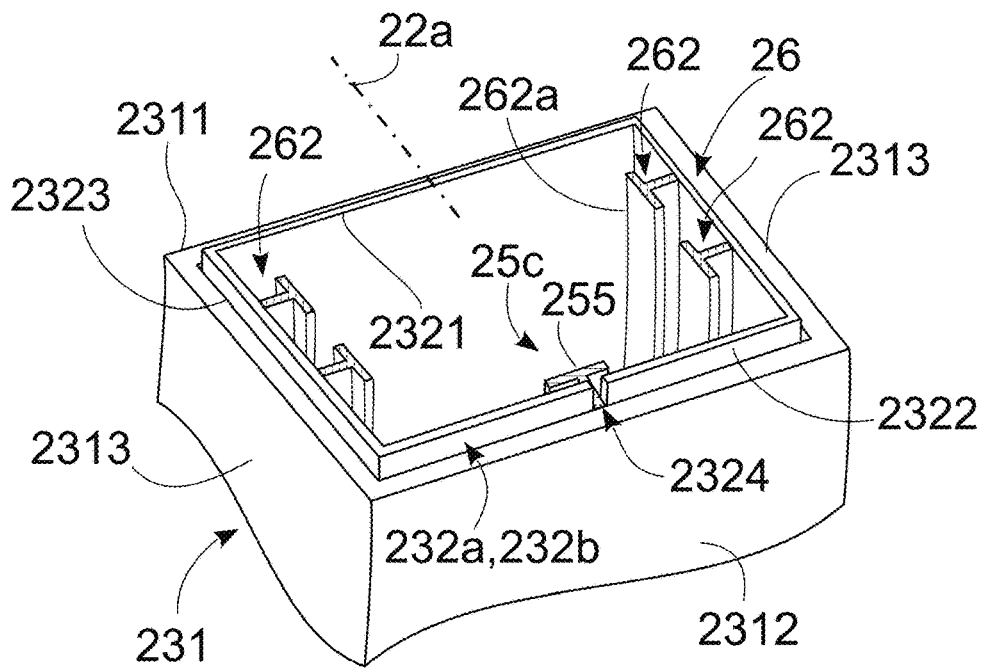
*Fig. 8a*
*Fig. 8b*
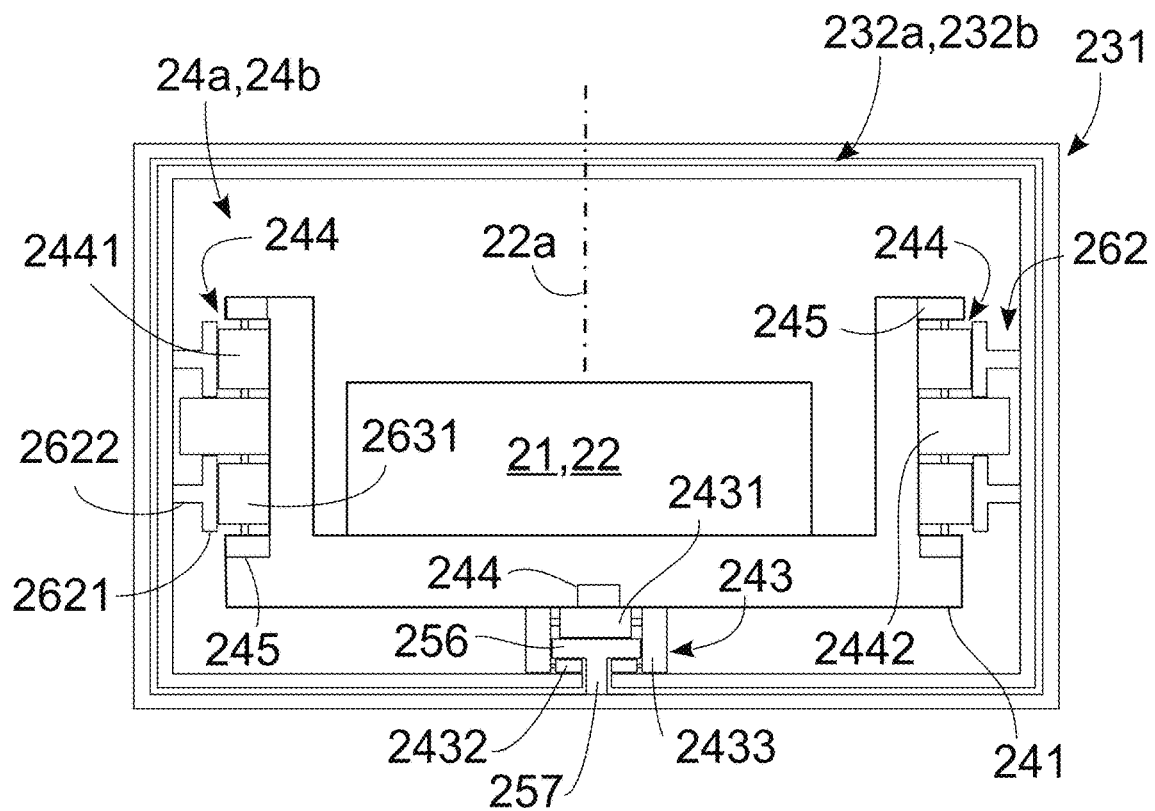

IMAGING DEVICE

CROSS-REFERENCE TO RELATED APPLICATIONS

This application claims priority to International Application No. PCT/IB2016/056461, filed Oct. 27, 2016, which claims priority to Italian Patent Application No. UB2015A005187, filed Oct. 29, 2015, and Italian Patent Application No. UB2015A004931, filed Oct. 29, 2015, each of which is incorporated by reference in its entirety.

FIELD OF THE INVENTION

The present invention relates to an imaging device. In particular, the present invention concerns a device suitable for use in the medical/veterinary sphere to obtain images of at least a portion of the internal anatomy of a patient and, thus, perform analyses, diagnoses or other examinations of said patient.

BACKGROUND

As is known, the imaging devices currently available on the market, regardless of the analysis to be performed (tomography, radiography or fluoroscopy), essentially have the same basic structure. Said structure comprises a bed on which the patient lies, a control station suitable to control the functioning of the device; an O-shaped gantry, defining a cavity inside which the portion to be analysed is placed and suitable to perform the imaging of the patient; and a support bearing the gantry and the bed that is able to reciprocally translate the bed and the gantry.

In detail, inside the gantry there are an X-ray source; a detector that receives the X-rays after these have traversed the bed and the patient.

Moreover, to perform image acquisition at different angles, measured in a plane perpendicular to the axis of the bed and thus of the patient, or tomography, the radiological device has a rotation mechanism that rotates the entire gantry or the source and the detector only around the patient to enable images to be acquired from different angles.

The prior art described above has a number of significant drawbacks.

A first significant drawback lies in the fact that the imaging devices currently available are particularly cumbersome.

The gantry, which must contain the source, the detector and the rotation mechanism, is particularly cumbersome. It has a diameter of at least 1.5 metres and cannot therefore be manoeuvred through doors or other openings present in hospitals.

For that reason, if, for example, imaging needs to be performed to verify the outcome of an operation, the patient must be lifted from the operating table, placed on a bed, moved to another part of the hospital to the room where the imaging device is installed, lifted again and then placed on the bed of the device.

This aspect is made worse by the fact that the source and the detector must be made to rotate with an angular amplitude of at least 360°, which requires the use of complex and laborious rotation mechanisms.

To overcome such problems, radiological devices have been developed which comprise a C-shaped gantry, known as a C-arm, consisting of a solid, curved, C-shaped body to the ends of which the source and detector are integrally connected; a specific rotation mechanism for rotating the entire C-arm has also been developed.

Although this solution partially overcomes the problems described above, it still has several important drawbacks.

Such imaging devices are, in fact, only able to make the source and detector rotate with a limited angular amplitude of not more than 200°.

Therefore, when performing a tomography scan, they are only able to acquire images at certain angles and so the reconstructed radiographic image is of poor quality and, thus, difficult for the physician to interpret.

Moreover, such imaging devices are often designed for a single function, usually only for fluoroscopy, and thus offer less functional flexibility.

Moreover, in view of their limited rotation, C-arm devices cannot acquire images from all angles around the patient.

It is important to note that the presence of these drawbacks considerably limits the use of C-arm gantry devices and therefore the imaging devices currently most widely used are those provided with an O-shaped gantry.

SUMMARY

In this situation the technical purpose of one embodiment of the present invention is to devise an imaging device able to substantially overcome the drawbacks mentioned above.

Within the sphere of said technical purpose one important aim of one embodiment is to obtain an imaging device which permits the patient to be manoeuvred easily and, above all, eliminates or reduces any risks to the patient without reducing the size of the acquisition angle.

Specifically, an important aim of one embodiment is to produce an imaging device with a reduced footprint and which, nonetheless, can be used to perform scans with an angular amplitude of at least 360°.

BRIEF DESCRIPTION OF THE DRAWINGS

The various embodiments will be now shown with the following description of an exemplary embodiment thereof, exemplifying but not limitative, with reference to the attached drawings in which:

FIG. 1a shows an imaging device according to one embodiment;

FIG. 1b is the imaging device in a configuration subsequent to that shown in FIG. 1a;

FIG. 1e is the imaging device in a configuration subsequent to that shown in FIG. 1d;

FIG. 2 illustrates a cross section of the imaging device according to one embodiment;

FIG. 4a presents a different embodiment of the assembly of FIG. 3a;

FIG. 4b illustrates a different arrangement of the assembly of FIG. 4a;

FIG. 7a shows a different embodiment of the assembly of FIGS. 3a and 4a;

FIG. 7b illustrates a different arrangement of the assembly of FIG. 7a;

FIG. 8a shows a detail of the assembly of FIG. 7a;

FIG. 8b illustrates a cross section of the assembly of FIG. 7a; and

DETAILED DESCRIPTION

Figure 1C:
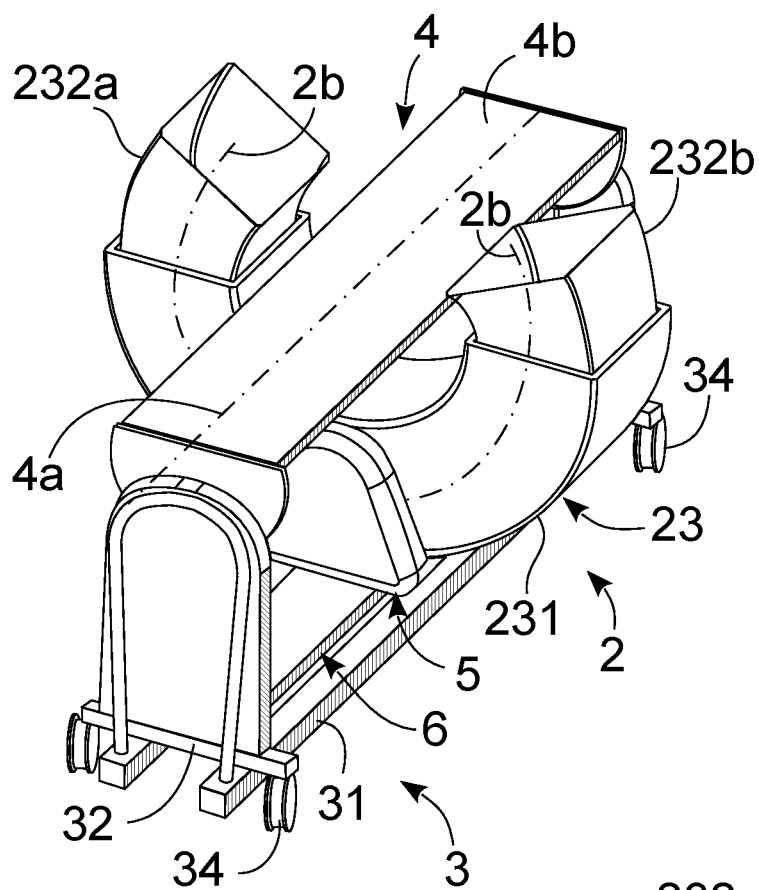
FIG. 1c presents the imaging device in a configuration subsequent to that shown in FIG. 1b.

In this document, measurements, values, forms and geometric data (such as perpendicularity and parallelism), when used with terms such as "about" or other similar terms such as "practically" or "substantially", are to be considered without any measurement errors or inaccuracies due to production and/or manufacturing errors and, above all, without any slight divergence from the value, measurement, form or geometric data with which they are associated. For example, such terms, when associated with a value, preferably indicate a difference of not more than 10% of said value.

Moreover, terms such as "first", "second", "upper", "lower", "main" and "secondary" do not necessarily indicate an order, priority or respective position, but may simply be used in order to make a clear distinction between the different components.

Unless otherwise specified, as is apparent from the description that follows, terms such as "processing", "computing", "determination", "calculation" or similar terms refer to the actions and/or processes of a computer or of a similar electronic calculation device which processes and/or converts physical data, such as the electronic quantities of computer system logs and/or memories, into other data also expressed as physical quantities in computer systems, logs or other data storage, transmission or display devices.

With reference to said drawings, reference numeral 1 globally denotes the imaging device according to one embodiment.

The device is suitable for use in the medical sphere (human/veterinary medicine) for performing imaging of at least a portion of the internal anatomy of a patient. In particular, the imaging device 1 is suitable for use in the medical sphere (human/veterinary medicine) for performing X-rays, computerised tomography, fluoroscopy and other imaging examinations.

Preferably, the imaging device 1 is a tomography device, that is to say, a device suitable to perform tomography and, appropriately, at least one from among computerised tomography (CT), single-photon emission tomography (SPECT) and/or positron emission tomography (PET).

The device 1 comprises a gantry 2 suitable to perform imaging; and, appropriately, a control unit 1a suitable to control the functioning of the device 1 and, precisely, of at least the gantry 2. The gantry 2 defines an analysis zone 2a suitable to contain at least the portion of the patient to be analysed and, appropriately, a circular trajectory of extension 2b extending around the analysis zone 2a and having its centre on a central axis 2c.

Note that in this description the terms "axial", "axially" and similar terms identify a direction substantially parallel to the central axis 2c, whereas the terms "radial", "radially" and similar terms identify a direction substantially perpendicular to the central axis 2c. The circular trajectory of extension 2b lies in a plane that is substantially perpendicular to the central axis 2c.

The gantry 2 may comprise an image acquisition unit suitable to perform radiological image acquisition and specifically at least one from among CT, SPECT, and PET. The image acquisition unit may comprise at least a detector 21 suitable to receive an emission after it has traversed at least part of the analysis zone 2a and, thus of the portion of the patient being analysed. Note that, at least in the case of SPECT and PET, the image acquisition unit may comprise several detectors 21.

A detector 21 comprises at least one sensor defining a surface sensitive to an appropriately radiological emission (X-rays for CT, photon emission for SPECT, positron emission for PET) and suitable to selectively perform, appropriately on the basis of a command sent by the operator, tomography, fluoroscopy and/or radiography. It therefore defines at least one sensitive surface suitable to detect the radiation and, specifically, substantially parallel to the central axis 2c.

Therefore, at least in the case of an imaging device 1 suitable to perform computerised tomography (CT) the sensor is suitable to perform at least said CT. Said sensor may therefore comprise at least one from among: a linear sensor and, preferably, two linear sensors defining substantially coplanar sensitive surfaces; a rectangular sensor, referred to as a flat panel sensor, preferably suitable to vary the area of the active sensitive surface; a direct photon counter sensor; a dual energy sensor; a concave sensor with the concavity facing the central axis 2c; a variable geometry sensor: flat or concave.

Appropriately, at least in the case of an imaging device 1 suitable to perform single-photon emission tomography (SPECT), the sensor may comprise a gamma camera. More appropriately, at least in the case of an imaging device 1 suitable to perform single-photon emission tomography (SPECT) the gantry 2 may comprise one or more detectors 21 (preferably two) each of which comprising a sensor suitable to perform at least said SPECT and which may be, for example, a CZT (Cadmium zinc telluride) or PMT (Photomultiplier tube) gamma camera.

Appropriately, at least in the case of an imaging device 1 suitable to perform positron emission tomography (PET), the sensor is suitable to perform at least said PET and may be, for example, a CZT (Cadmium zinc telluride) or PMT (Photomultiplier tube) gamma camera. Note that in some cases the detector 21 may comprise a combination of said sensors and, for example, a SPECT and/or PET sensor and a CT sensor.

The detector 21 may comprise at least one lateral and/or vertical movement apparatus and, in detail, at least one from among a shifting assembly suitable to translate the sensor along a shifting axis and a lifting assembly suitable to translate the sensor along a lifting axis practically normal to the shifting axis. The shifting assembly is provided with a slider connected to the sensor, a shifting guideway defining the shifting axis and a motor, specifically an electric motor, to control the motion of the slider on the shifting guideway. The shifting axis is substantially perpendicular to the central axis 2c and, appropriately, tangential to the circular trajectory of extension 2b.

The lifting system comprises a linear actuator, preferably electric, suitable to move the sensor and, preferably, the shifting assembly along the lifting axis. The lifting axis is practically perpendicular to the central axis $2c$. At least in the case of an imaging device 1 suitable to perform computerised tomography (CT) the image acquisition unit may comprise at least one source 22. In the case of SPECT and PET, the source 22 may not be present.

The source 22 may be suitable to emit radiation, preferably X-rays, defining a central axis of propagation 22*a* preferably practically perpendicular to the sensitive surface of the detector 21, and thus, to the central axis $2c$. The source 22 may comprise an X-ray emitter defining the central axis of propagation 22*a* and, optionally, a tilting mechanism suitable to rotate the X-ray emitter and, thus, the central axis of propagation 22*a*, appropriately about a tilting axis practically parallel to the central axis $2c$, and appropriately passing through the focal spot of the emitter so as to maintain the focal spot practically still.

The gantry 2 may comprise a casing 23 that defines a housing volume for at least the source 22, the detector 21 and substantially extends along the circular trajectory of extension 2*b*; and preferably a movement apparatus suitable to move the detector 21 and the source 22, if present, inside the housing volume defined by the casing 23. The casing 23 is suitable to always contain one or more detectors 21 and, if present, the source 22. Appropriately, the casing 23 is suitable to also always contain the movement apparatus of the at least one detector 21 and of the source 22, if present. The gantry 23 constitutes the outside of the gantry 2 and, thus, defines the overall dimensions and, in particular, the angular extension of the gantry 2 and of the circular trajectory of extension 2*b*.

The casing 23 and, thus, the gantry 2 are of the telescopic type, that is suitable to vary their angular extension along the circular trajectory of extension 2*b* so as to define at least one rest configuration and at least one working configuration of the gantry 2. In the rest configuration (FIGS. 1*a*-1*b*, 2, 3*a*, 4*a* and 7*a*) the casing 23 and the gantry 2 are contracted and have a minimum angular extension. Therefore, the casing 23, the gantry 2 and, thus, the circular trajectory of extension 2*b* define an arc of a circumference substantially centred on the central axis $2c$ and having a minimum angular extension with an angular amplitude of practically less than 260° and, in detail, less than 210° and, more in detail, substantially equal to 190°.

In the at least one working configuration (FIGS. 1*c*-1*e*, 3*b*, 3*c*, 4*b*-4*e*, 7*b*), the casing 23 and the gantry 2 have a circular trajectory of extension 2*b* with a greater angular extension than said minimum angular extension so as to at least partially surround at least a larger portion of the analysis zone 2*a* to allow the source 22 and the detector 21 to position themselves on opposite sides with respect to the central axis $2c$ and, thus, the analysis zone 2*a*. Specifically, the gantry 2 defines a fully extended working configuration (FIGS. 1*d*, 1*e*, 3*b*, 3*c*, 4*b*-4*e*, 7*b*), in which the casing 23 and, thus, the gantry 2 are practically closed so as to define a circular trajectory of extension 2*b* with an angular extension of 360° and thus an O-shaped gantry 2 enclosing and, appropriately, laterally delimiting the entire analysis zone 2*a*. Note that the gantry 2 (and thus the casing 23) move from one configuration to the other while always maintaining the at least one detector 21 and, if present, the source 22, inside the casing 23 irrespectively of the angular extension of the casing 23. Preferably, the gantry 2 changes configuration while also always maintaining the movement apparatus inside the casing 23.

Optionally, in some cases, if the sensor is moved by the lifting system so that its travel exceeds a predefined maximum limit, the detector 21 may come out of and at least partially protrude from the casing 23. Therefore, to allow the lifting system to translate the sensor along the lifting axis, the casing 23 may be provided with a window facing the analysis zone 2*a* through which the sensor is able to protrude from the casing 23 when translated along the lifting axis.

In order to achieve said configurations, the casing 23 comprises at least two or more substantially hollow curved modules so as to define the housing volume and which are reciprocally movable so as to vary the extension of the casing 23. The curved modules have substantially the same barycentric axis which practically coincides with the circular trajectory of extension 2*b*. They have different cross sections so as to enable their reciprocal insertion and/or superimposition.

In detail, the casing 23 comprises one, preferably only one, curved base module 231 and at least one curved module that is movable relative to the curved base module 231 so as to vary the angular extension of the casing 23 and of the gantry and, thus, of the housing volume. More in detail, the casing 23 comprises a curved base module 231, a first curved mobile module 232*a* and a second curved mobile module 232*b* arranged at the end of the curved base module 231 opposite to that of the first curved mobile module 232*a* and preferably substantially specular with respect to said first curved mobile module 232*a*. Note that the mobile modules 232*a* and 232*b* can be moved dependently (simultaneously at substantially the same speed and in opposite directions) and independently.

In order to have an O-shaped gantry 2, in the fully extended working configuration, the sum of the angular amplitudes of the modules 231, 232*a* and 232*b* is at least equal to 360°. Preferably, said sum of the angular amplitudes of the modules 231, 232*a* and 232*b* is at least equal to 370° so as to always have an area in which the curved mobile modules 232*a* and 232*b* are superimposed on the curved base module 231 in order to guarantee the structural stability of the gantry 2.

The curved base module 231 has an angular extension that is practically less than 240° and, more in particular, substantially less than 210° and, yet more in particular, substantially comprised between 190° and 160°. Each curved mobile module 232*a* and 232*b* has an angular extension that is practically less than 140° and, preferably, practically less than 120° and, yet more preferably, substantially comprised between 100° and 80°.

The curved mobile modules 232*a* and 232*b* have a cross section that is different from that of the curved base module 231 so as to be at least partially superimposed on the curved base module 231 and, advantageously, vary the extension of the part of the mobile module 232*a* and 232*b* superimposed on the curved base module 231 during a change of configuration. Preferably, the curved mobile modules 232*a* and 232*b* have a cross section that is smaller than that of the curved base module 231 so as to be housed therein and, advantageously, vary the extension of the part of the curved mobile module 232*a* and 232*b* housed inside the curved base module 231 during a change of configuration.

Preferably, in the rest configuration each curved mobile module 232*a* and 232*b* is entirely superimposed and, precisely, housed inside the curved base module 231 so that the angular extension of the gantry 2 is equal to that of the curved base module 231. More preferably, in the rest configuration the curved mobile modules 232a and 232b are in the curved base module 231 and substantially in contact with one another.

In the at least one working configuration, at least one of the curved mobile modules 232a and 232b and, in particular, both of the mobile modules 232a and 232b protrude at least partially from the curved base module 231 so that the angular extension of the gantry 2 is greater than that of the curved base module 231. In detail, in the at least one working configuration the angular extension of the gantry 2 is practically equal to the angular extension of the curved base module 231 plus the angular extension of each portion of curved mobile module 232a and 232b protruding from the curved base module 231.

In order to stably block the curved modules 231, 232a and 232b together in any position with respect to the curved base module 231 and, thus, the gantry 2 in any configuration, the gantry 2 comprises at least one retainer, available on the inside of the casing 23, which defines a locked position in which it prevents the relative motion between the curved modules 231, 232a and 232b and a released position in which it permits the relative motion between the curved modules 231, 232a and 232b.

In particular, the gantry comprises a first retainer suitable to selectively define said locked and released positions between the first mobile module 232a and the curved base module 231 and a second retainer suitable to selectively define said locked and released positions between the second curved mobile module 232b and the curved base module 231.

Each retainer consists of a linear actuator integral with a curved mobile module 232a or 232b defining a high friction contact surface with the curved base module 231 and suitable to vary its length, appropriately in a direction substantially radial with respect to the circular trajectory 2b so that, in the locked position, the contact surface presses against the curved base module 231 so as to integrally connect the curved modules 231, 232a and 232b together, while in the released position the contact surface is moved away from the curved base module 231 to permit a reciprocal sliding between said modules. The curved modules 231, 232a and 232b are defined by hollow curved profiles.

Appropriately (as illustrated in FIG. 8a), the curved base module 231 comprises a proximal base plate 2311 with respect to the central axis 2c extending practically in a circle with its centre on the central axis 2c; a distal base plate 2312 with respect to the central axis 2c extending in a circle with its centre on the central axis 2c and with a radius greater than that of the proximal base plate 2311; and, appropriately subtended between the base plates 2311 and 2312, two lateral base plates 2313 extending practically transversely and, in particular, perpendicularly to the central axis 2c and, appropriately, arranged on opposite sides with respect to the base plates 2311 and 2312.

Likewise (FIG. 8a), each curved mobile module 232a and 232b comprises a proximal mobile plate 2321 with respect to the central axis 2c extending practically in a circle with its centre on the central axis 2c; a distal mobile plate 2322 with respect to the central axis 2c extending in a circle with its centre on the central axis 2c and with a radius greater than that of the proximal mobile plate 2321; and, appropriately subtended between the curved plates, two lateral mobile plates 2323 extending practically transversely and, in detail, perpendicularly to the central axis 2c and, appropriately, arranged on opposite sides with respect to the mobile plates 2321 and 2322.

To rotate the source 22 and the detector 21 about the analysis zone 2a, the gantry 2 comprises, arranged in the housing volume regardless of the configuration of the gantry 2 and thus of the angular extension of the casing 23, the movement apparatus of the at least one detector 21 and of the source 22, if present. The movement apparatus may comprise, appropriately inside the casing 23, at least one carriage to which the transported unit (consisting of the image acquisition unit and, precisely, the detector 21 and/or the source 22) to be moved with respect to the casing 23 is fixed. Preferably, the movement apparatus may comprise several carriages so that the components of the image acquisition unit, i.e., the one or more detectors 21 and the source 22, if present, can be moved separately and independently.

For example, in the case of an imaging device 1 for performing at least SPECT and PET, the gantry 23 may comprise one or more detectors 21 and the movement apparatus may comprise one carriage to which all the detectors are fixed or, alternatively, one carriage for each detector 21. Therefore, in the case of an imaging device 1 for PET or preferably SPECT, the gantry 23 may comprise two detectors 21 and the movement apparatus may comprise a first carriage 24a to which one detector 21 is connected and a second carriage 24b to which the other detector 21 is connected.

In another example of an imaging device 1 for CT, the gantry 23 may comprise a detector 21 and a source 22 and the movement apparatus may comprise a first carriage 24a to which the source 22 is connected and a second carriage 24b to which the detector 21 is connected. In a further example of an imaging device 1 for CT and at least one from between SPECT and PET, the gantry 23 may comprise a source 22 and one or more detectors 21 and the movement apparatus may comprise a carriage for the one source 22 and a carriage for each detector 21. Therefore, in this case the gantry 23 may comprise one source 22 and two detectors 21 and the movement apparatus may comprise a first carriage 24a to which one detector 21 is connected, a second carriage 24b to which the other detector 21 is connected and a third carriage, identical to the previous ones, for the source 22.

Each carriage 24a and 24b is suitable to define along the circular trajectory of extension 2b two opposite ends, that is to say, a head end and a tail end. The at least one carriage 24a and 24b extends mainly substantially along the circular trajectory of extension 2b and its overall dimensions may be substantially smaller than those of the portion of housing volume defined by the curved mobile modules 232a and 232b so as to be arranged completely inside the latter. In particular, one carriage 24a and/or 24b has an angular extension substantially comprised between 10° and 80° and, more in particular, between 20° and 40°. A carriage 24a and/or 24b comprises a support 241 for the unit being transported, defined by an appropriately curved plate that extends along the circular trajectory of extension 2b.

Figure 5:
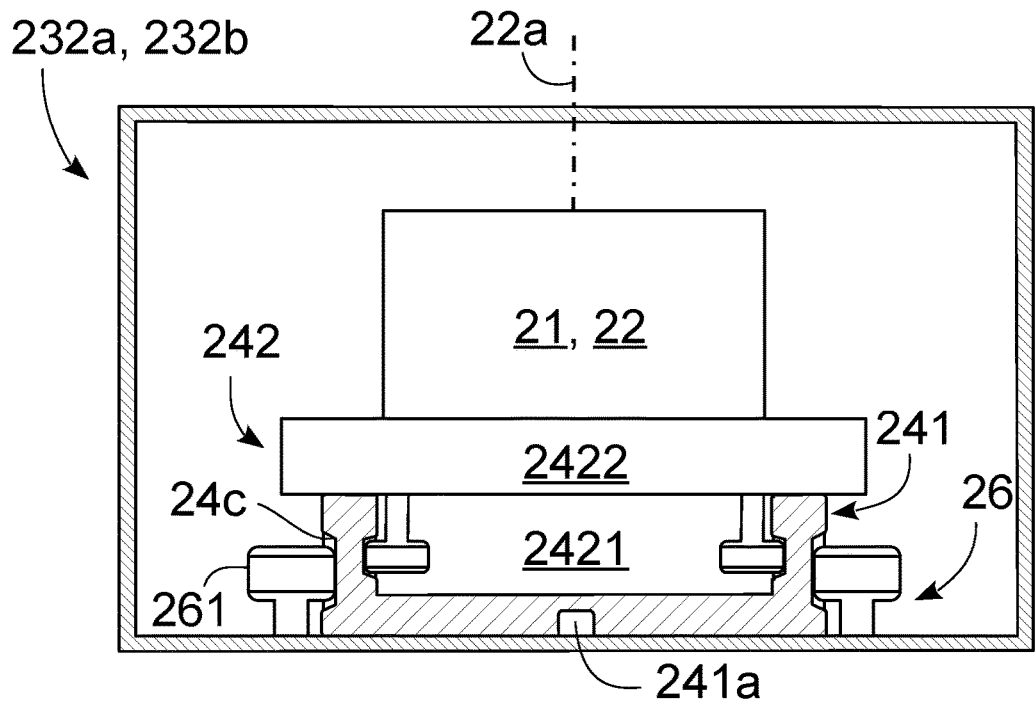
FIG. 5 is a cross section of the imaging device.

The support 241 may be integral with the unit being transported. Alternatively, the at least one carriage 24a and/or 24b may comprise (FIG. 5) a relative sliding module 242 suitable to support the unit being transported by said carriage and to make the unit being transported slide with respect to the support 241 preferably along a circular trajectory concentric to the central axis 2c and, in detail, along the circular trajectory of extension 2b.

The relative sliding module 242 comprises a guiding member 2421 which is integral with the support 241 and defines a relative sliding direction that substantially coincides with the circular trajectory of extension 2b; a carrier 2422 integral with the unit being transported and which engages with the guiding member 2421 to determine said sliding. The guiding member 2421 is defined by a groove obtained in the support 241 and appropriately extending substantially along the circular trajectory of extension 2b. The guiding member 2421 and, specifically, the groove, are toothed so as to define a rack mechanism and, therefore, the carrier 2422 may comprise a motorised toothed wheel, that engages with said rack and is hinged to said carrier 2422. Alternatively, the groove and, thus, the guiding member 2421, have a smooth surface with which the carrier engages and the carrier 2422 comprises a motorised friction wheel hinged to the carrier 2422, i.e., a wheel suitable to engage with said smooth surface and exploit the force of friction between the wheel and said smooth surface to move the carrier 2422.

To allow the at least one carriage 24a and/or 24b to slide inside the entire casing 23 and around the analysis zone 2a, the movement apparatus may comprise a base guideway 25 integral with and inside the curved base module 231 and defining a base sliding trajectory 25a for the at least one carriage 24a and/or 24b within the curved base module 231; and a mobile guideway 26 integral with and inside the at least one curved mobile module 232a and/or 232b and defining a mobile sliding trajectory 26a for the at least one carriage 24a and/or 24b within the curved mobile module 232a and/or 232b.

It is important to note that the guideways 25 and 26 can move the at least one carriage 24a and/or 24b with respect to the casing 23 and, precisely, with respect to the curved modules 231, 232a and 232b which thus remain stationary during said movement of the at least one carriage 24a and/or 24b. Optionally, the base guideway 25 may move the at least one mobile module 232a and/or 232b during a change of configuration of the gantry 2.

The sliding trajectories 25a and 26a are circular and preferably concentric to the central axis 2c. When the gantry 2 is in the working configuration, each of the sliding trajectories 25a and 26a defines the extension of the other. They may therefore coincide and, thus, have the same radius, calculated with respect to the central axis 2c, and the same position along the central axis 2c, that is, the trajectories 25a and 26a lie in planes that intersect the central axis 2c at two different points. Optionally, the circular sliding trajectories 25a and 26a practically coincide with the circular trajectory of extension 2b.

Alternatively, the mobile sliding trajectory 26a may differ from the base sliding trajectory 25a in that it has a different radius and/or a different position on the central axis 2c so that, during a change of configuration of the gantry 2 the guideways 25 and 26 slide reciprocally. In detail, in the at least one working configuration only a limited portion of the mobile guideway 26 is arranged in the curved base module 231, and, thus, it is only partially superimposed on the base guideway 25, whereas in the fully extended working configuration no part of the mobile guideway 26 is inside the curved base module 231, and thus, it is not superimposed on the base guideway 25. Preferably, the mobile sliding trajectory 26a differs from the base sliding trajectory 25a because it has a different radius and a different position along the central axis 2c.

The guideways 25 and 26 may be obtained in plates of the modules 231, 232a and 232b parallel to one another and at a minimum distance in the rest configuration as shown in FIG. 8a. Alternatively, the guideways 25 and 26 may be obtained in plates of the modules 231, 232a and 232b that are not parallel to one another or opposite one another.

The circular sliding trajectories 25a and 26a permit the at least one carriage 24a and/or 24b and, thus, the unit being transported (source 22 and/or detector 21) to rotate about the analysis zone 2a and, in particular, about the central axis 2c at any angle (even angles of more than 360°). The sum of their angular extensions is thus substantially at least equal to 360° and, in some cases, at least equal to 370° so that, in at least one angular sector of the gantry 2, there is always an area of superimposition in which both of the guideways 25 and 26 are present. In particular, the guideways 25 and 26 may define, between the first curved module 232a and the curved base module 231, a first area of superimposition 26d of the guideways 25 and 26 and, between the second curved mobile module 232b and the curved base module 231, a second area of superimposition 26e of the guideways 25 and 26.

The base guideway 25 may be active, that is appropriately motorised so as to control the sliding of the carriage 24a and/or 24b along the base sliding trajectory 25a, or alternatively passive and, thus, it is the carriage 24a and/or 24b that is motorised. The base guideway 25 may comprise at least a slider 25b (FIGS. 3a-4e) housed in the curved base module 231 and defining the base sliding trajectory 25a. In particular, the base guideway 25 comprises two or more sliders 25b suitable to move independently of one another. One slider 25b is suitable to engage with the carriage 24a and/or 24b and maintain it not in contact with the curved base module 231 so as to define a minimum distance between the carriage 24a and/or 24b and the curved base module 231 at least equal to the thickness of the curved mobile modules 232a and 232b. One slider 25b has a main trajectory of extension that practically coincides with the base sliding trajectory 25a and, thus, with the circular trajectory of extension 2b. Preferably, the slider 25b has an angular amplitude that is substantially smaller than the difference between the angular extension between the curved base module 231 and the total angular extension of the curved mobile modules 232a and 232b. In detail, said angular amplitude of the slider 25b is less than 20°, in particular, less than 10° and, more in particular, substantially comprised between 8° and 5°.

It is characterised by overall dimensions that are substantially smaller than those of the curved base module 231 so as to be arranged inside the latter and, appropriately, not smaller than those of the mobile modules 232a and 232b, and to advantageously abut against said curved mobile modules 232a and 232b.

Figure 3A:
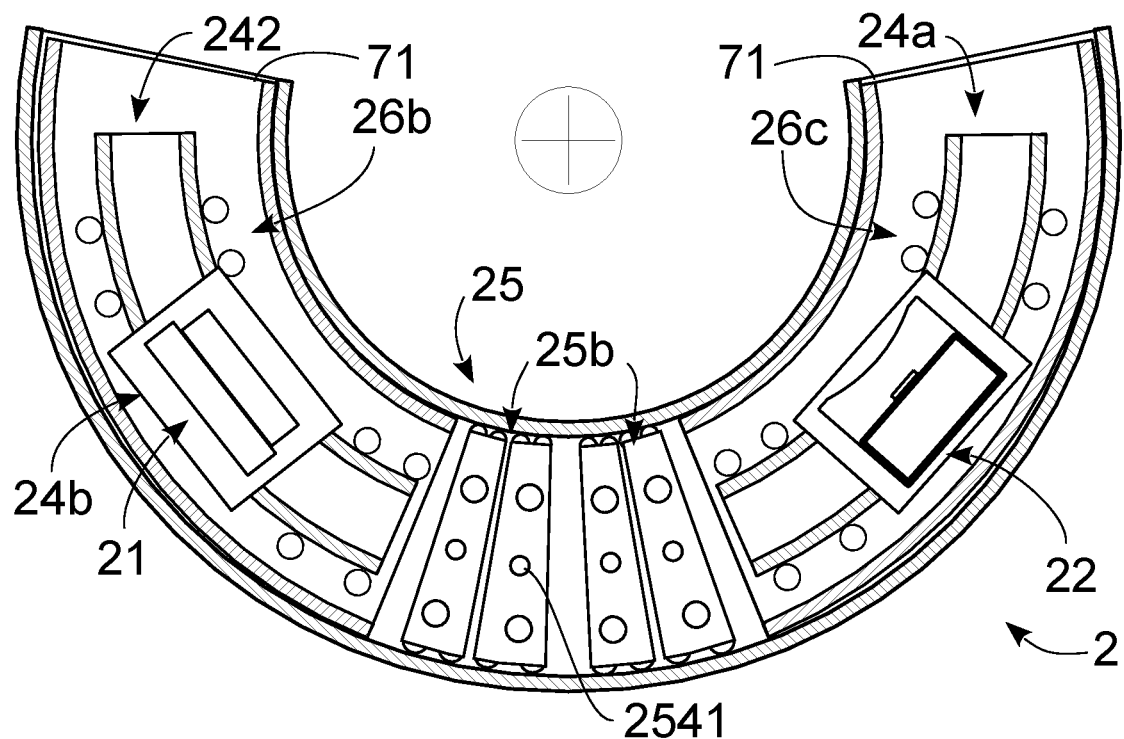
FIG. 3a shows a cross section of an assembly of the imaging device according to one embodiment.
Figure 3B:
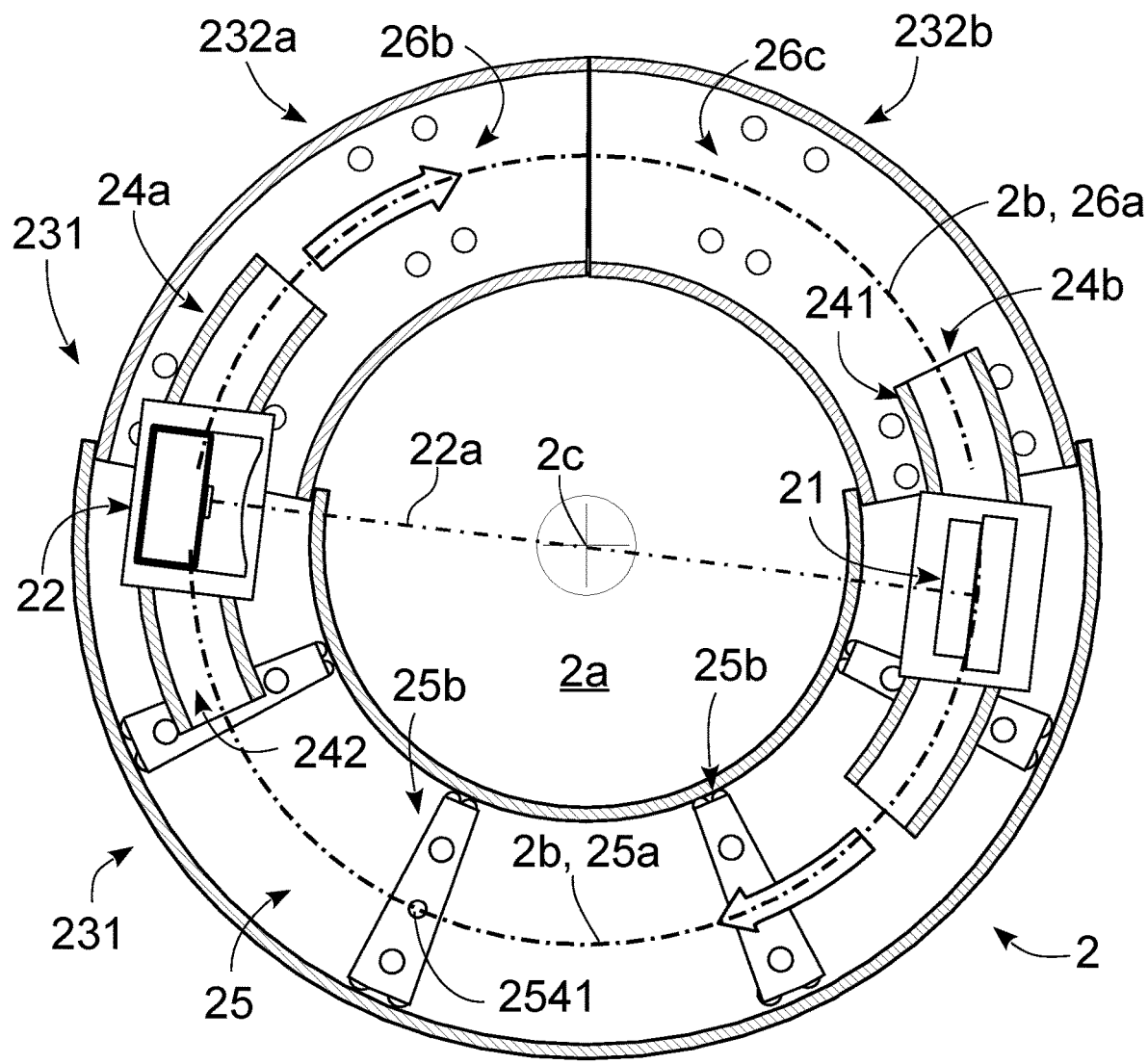
FIG. 3b shows the assembly of FIG. 3a in a different moment of use.
Figure 3C:
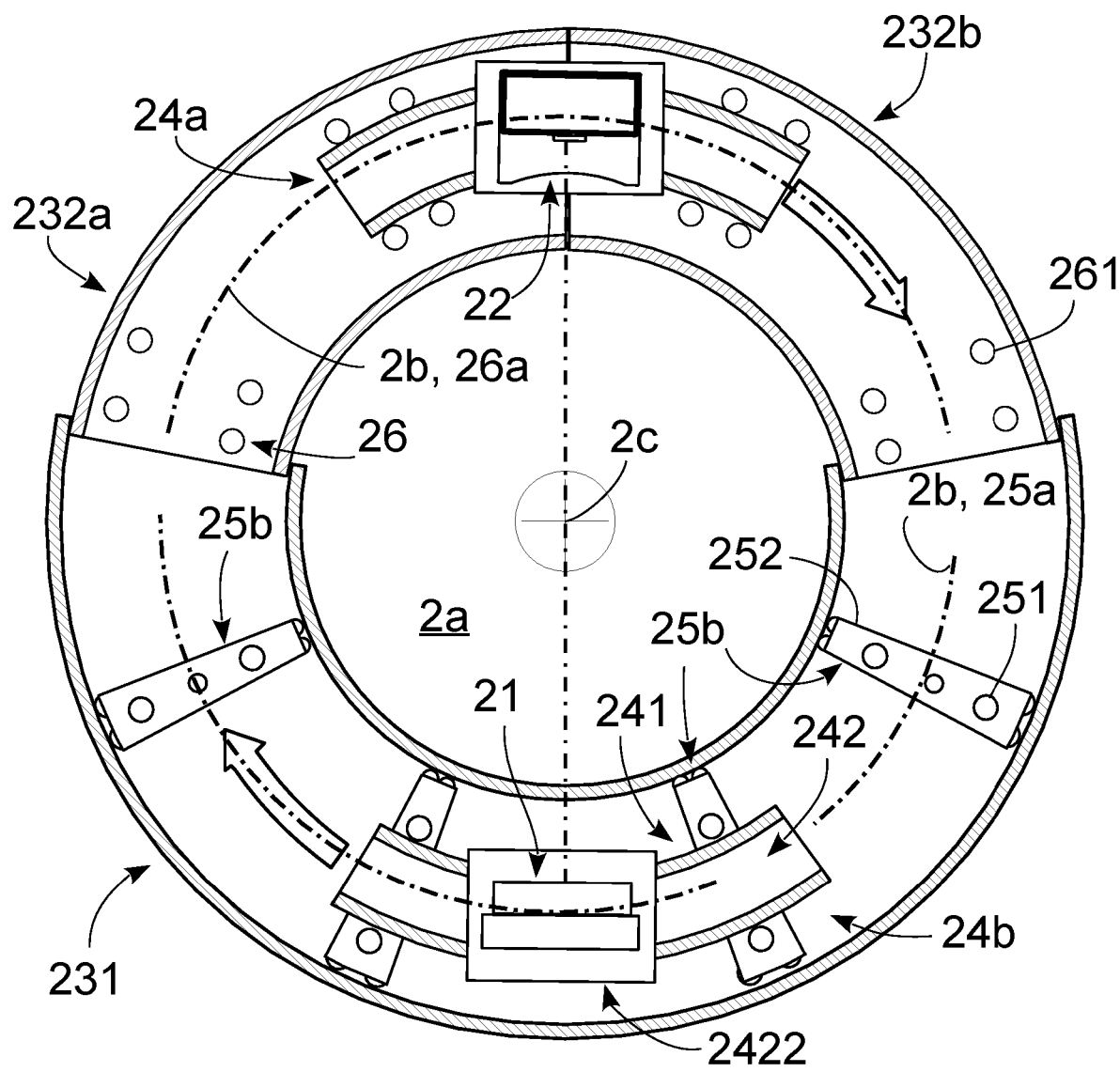
FIG. 3c is the assembly of FIGS. 3a and 3b in another moment of use.
Figure 4B:
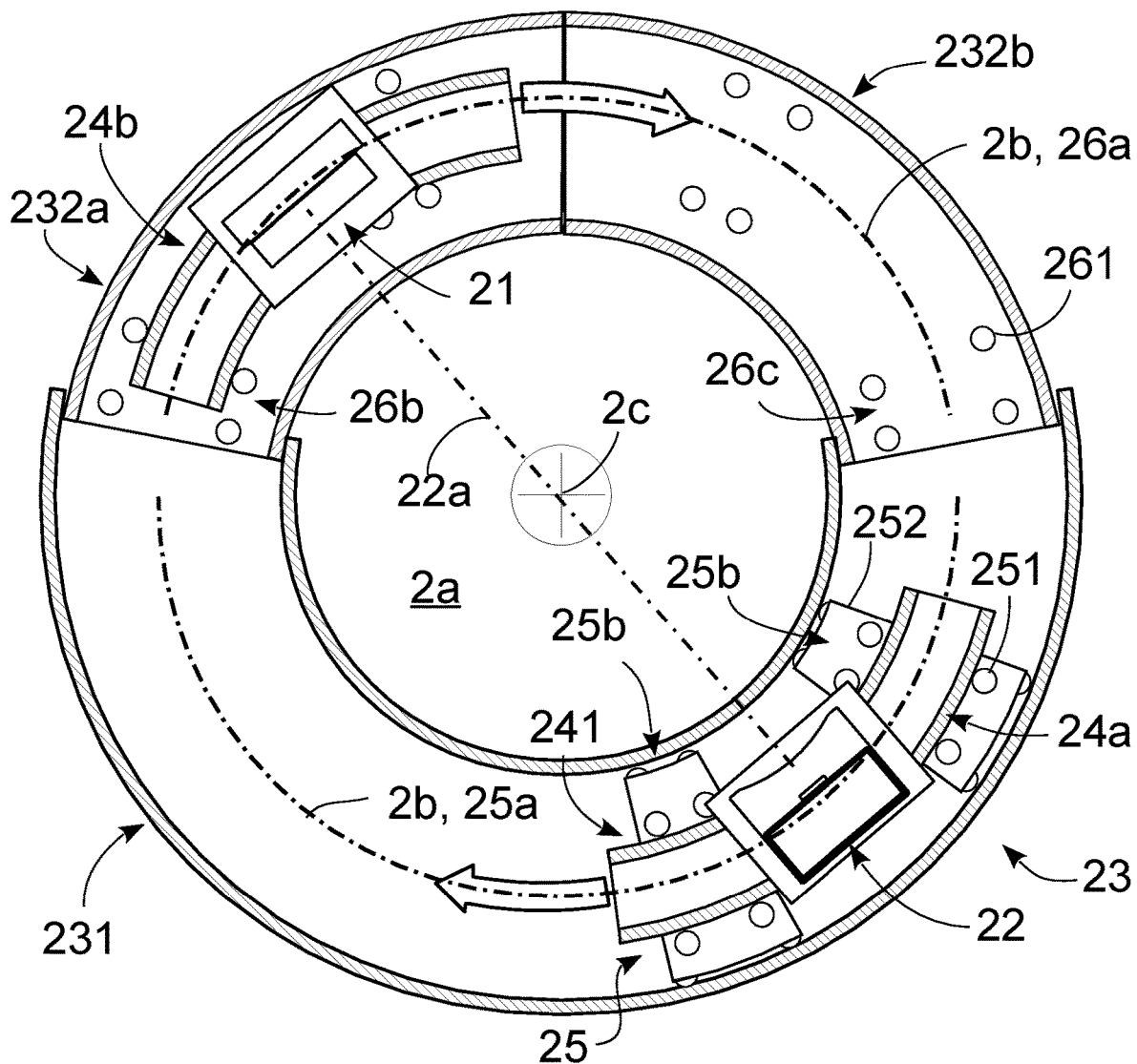
Figure 4C:
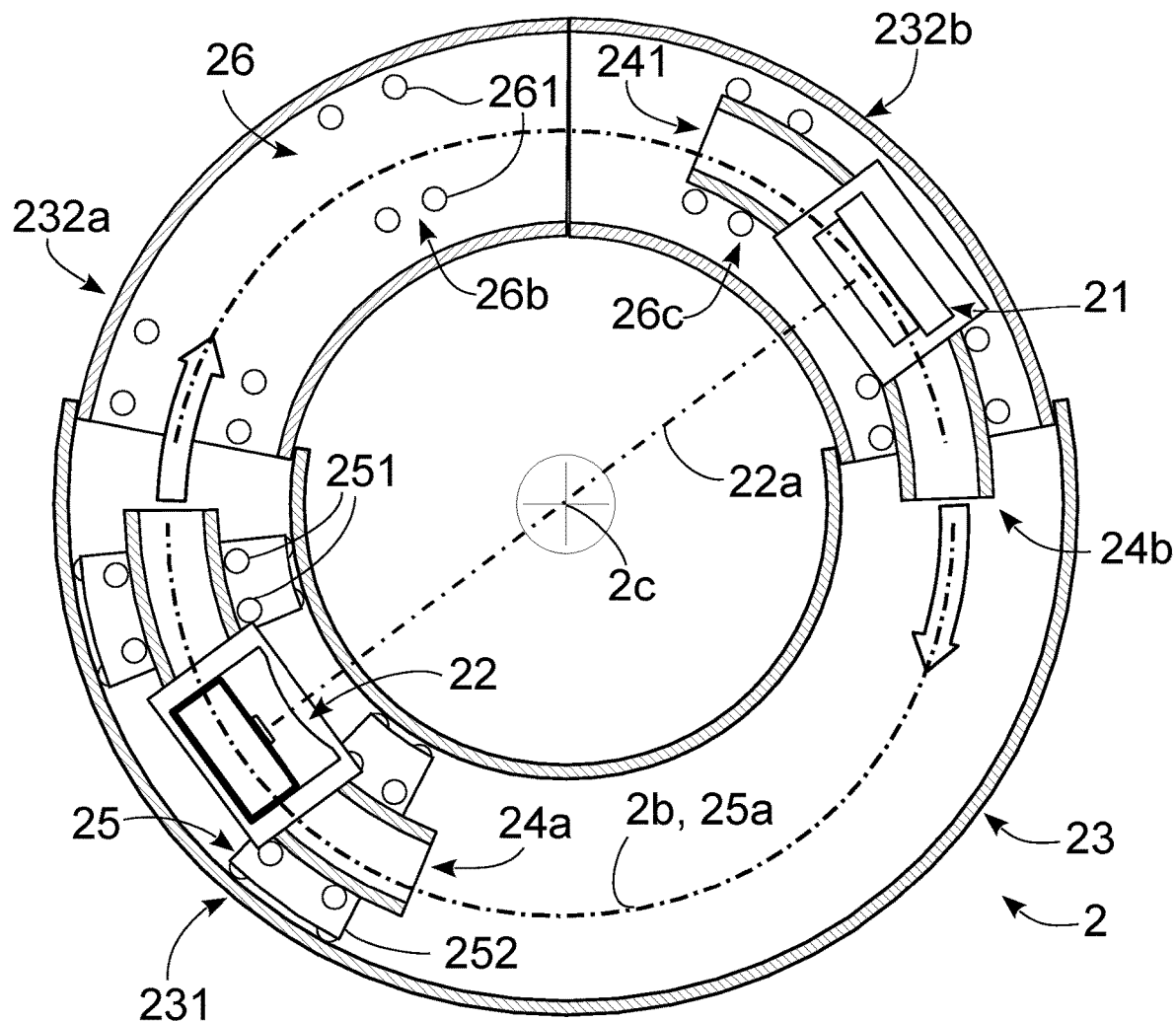
FIG. 4c shows a further arrangement of the assembly of FIGS. 4a and 4b.
Figure 4D:
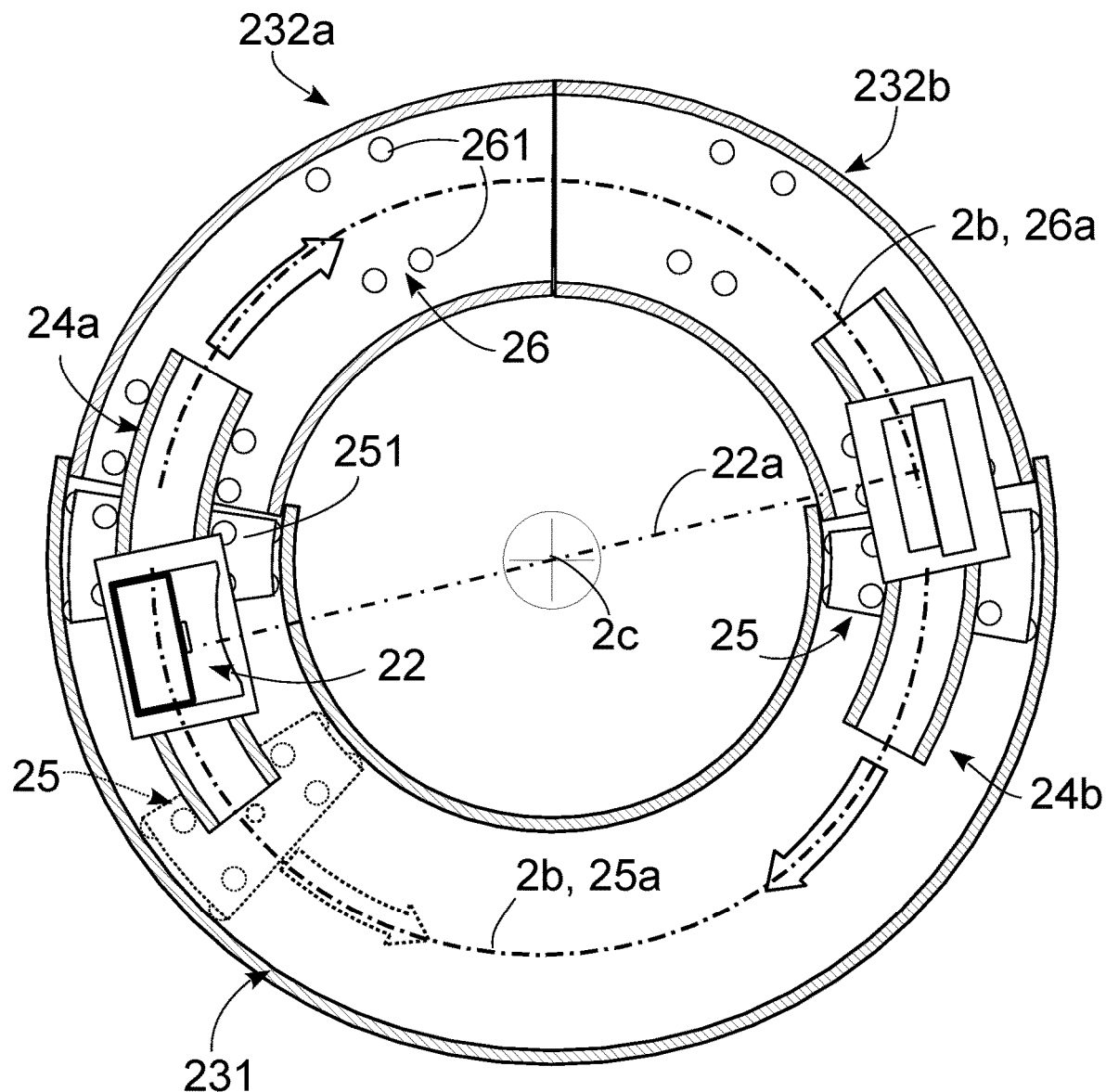
FIG. 4d is a specific arrangement of the assembly of FIGS. 4a-4c.
Figure 4E:
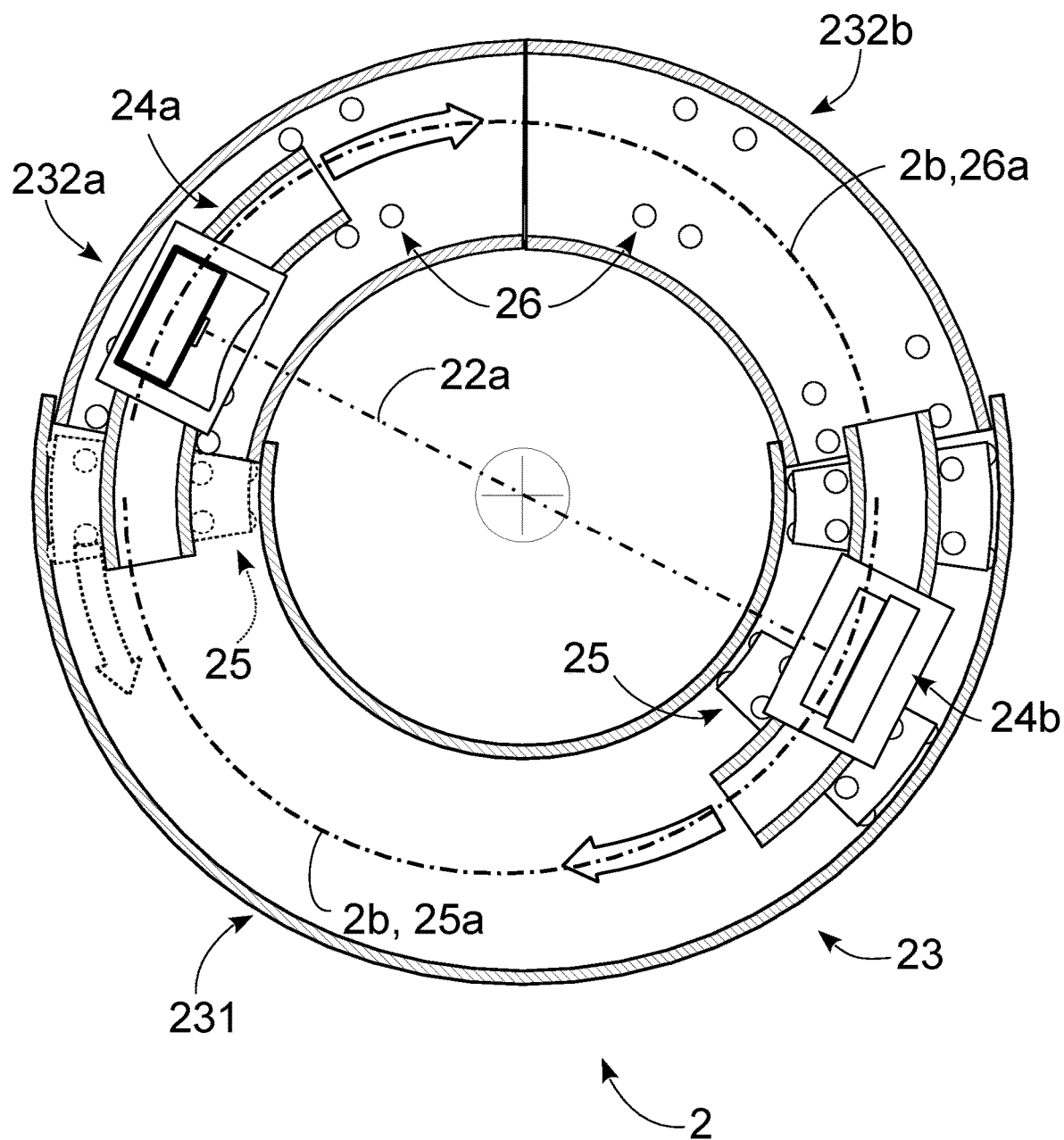
FIG. 4e is an additional arrangement of the assembly of FIGS. 4a-4d.
Figure 6:
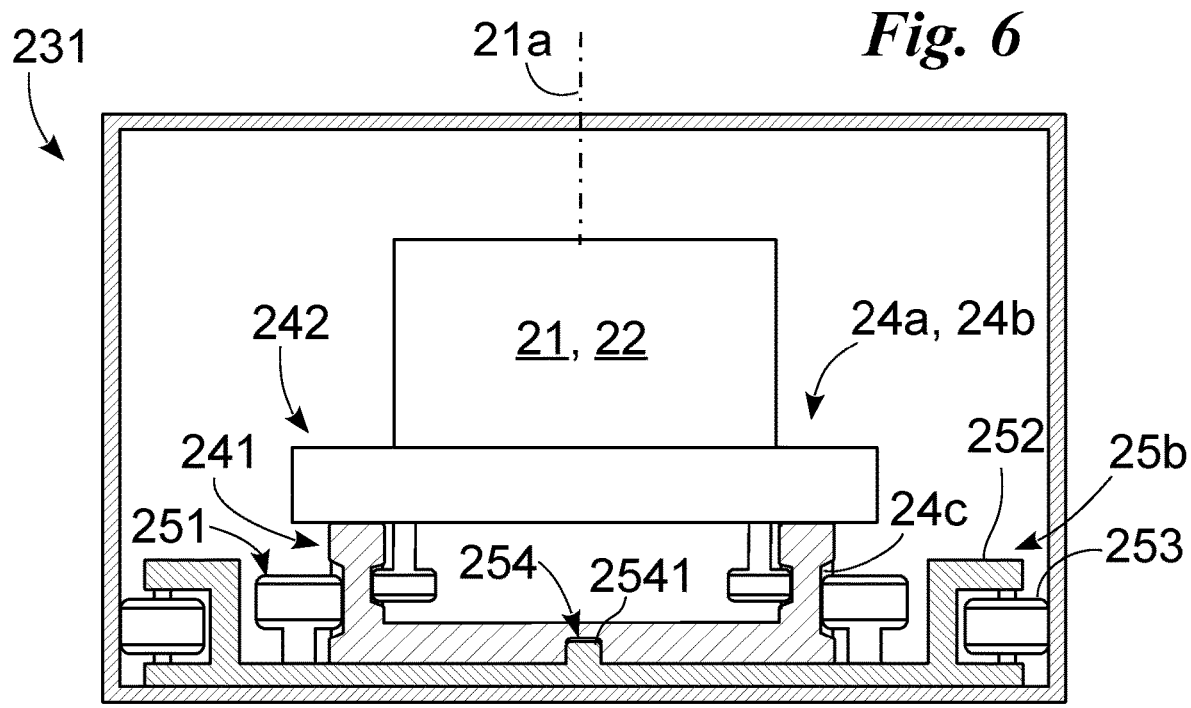
FIG. 6 is a different cross section of the imaging device.
Figure 7A:
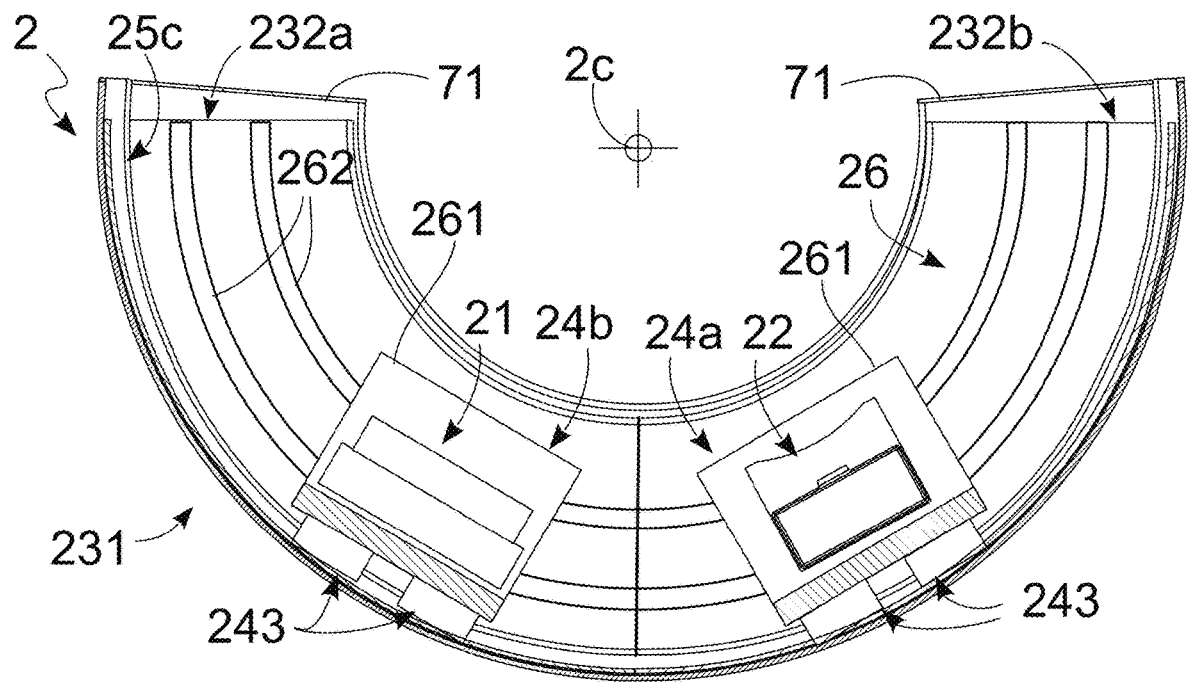
Figure 9:
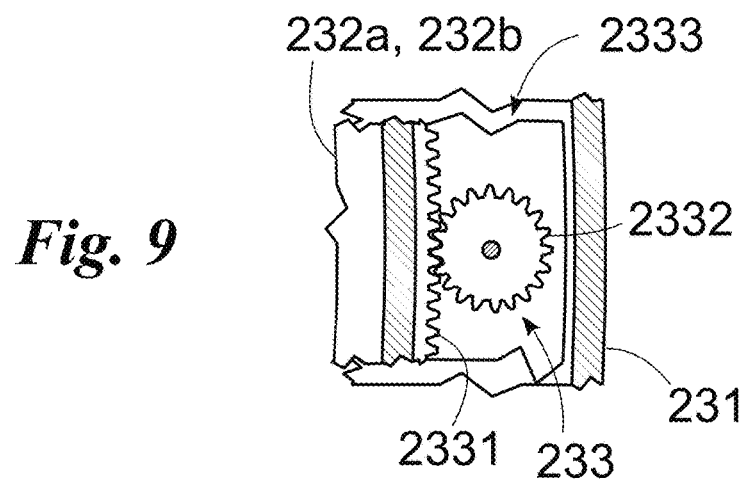
FIG. 9 shows a detail of the imaging device according to one embodiment.
Figure 7B:
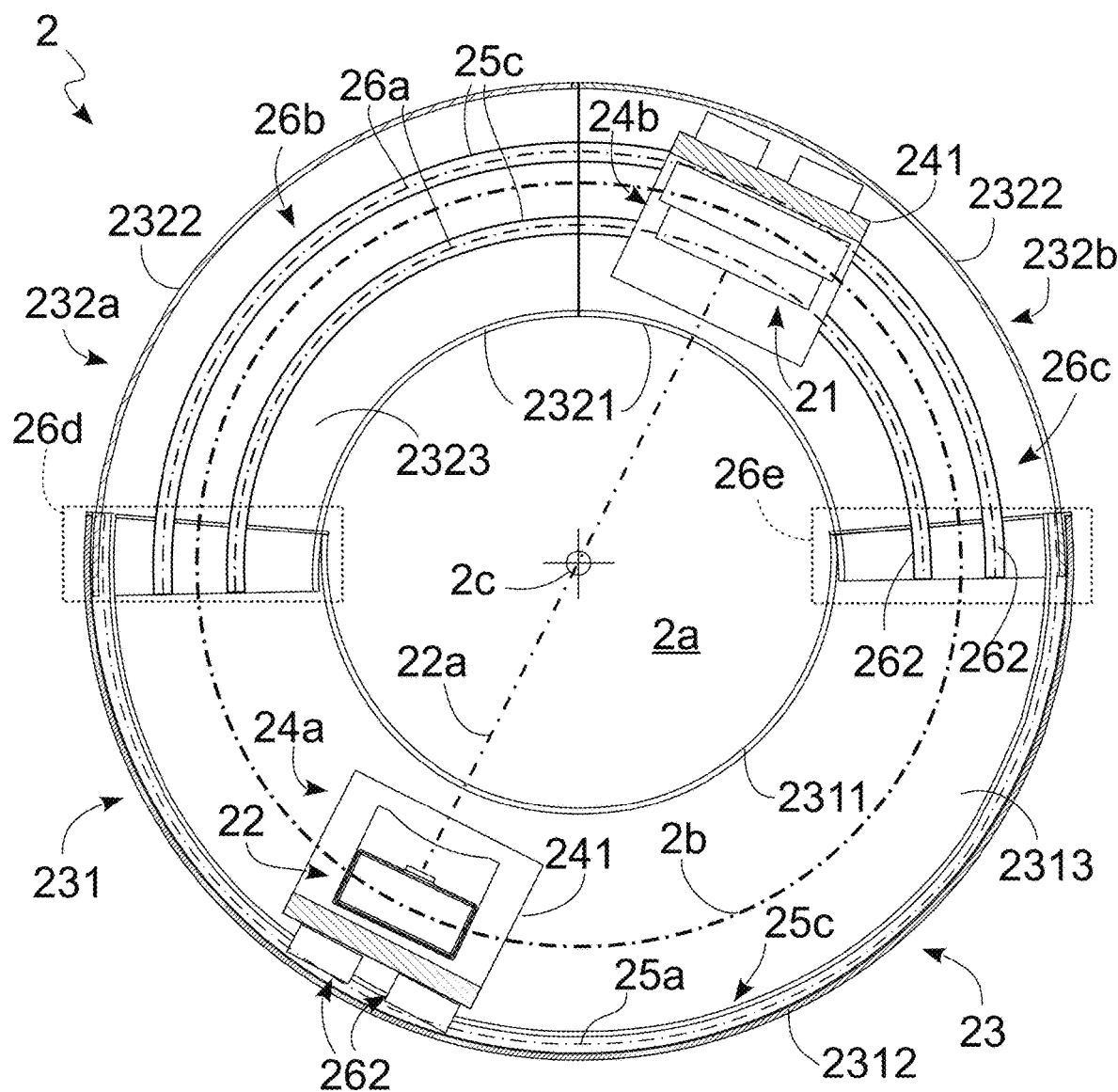

Each slider 25b comprises engagement means 251 suitable to engage the at least one carriage 24a and/or 24b with the slider 25b; and appropriately, a support 252 for the engagement means 251 (FIGS. 3c and 6). The engagement means 251 are suitable to engage the carriage 24a and/or 24b with the support 252 and, preferably, to permit the carriage 24a and/or 24b to slide with respect to the slider 25b. The base guideway 25 may be active and, thus, the engagement means 251 may comprise at least one or more movement wheels suitable to engage with the at least one carriage 24a and 24b, appropriately in correspondence with at least one engagement surface 24c obtained on the at least one carriage 24a and 24b, and to push and move said carriage 24a and/or 24b along the base sliding trajectory 25a.

In the case of a base guideway 25 suitable to move the at least one mobile module 232a and/or 232b, said engagement means 251 are suitable to engage with said at least one mobile module 232a and/or 232b which, thus, may comprise an additional engagement surface identical to an engagement surface 24c. The movement wheels are hinged to the support 252 and appropriately motorised. The engagement surface 24c is appropriately obtained on a surface of the support 241 substantially concentric to the central axis 2c. The engagement surface 24c may be toothed and, thus, the movement wheels may be toothed wheels. Alternatively, the engagement surface 24c may be smooth and, thus, the movement wheels may be friction wheels, that is wheels suitable to engage with a smooth engagement surface 24c and to exploit the friction force between the wheel and said smooth engagement surface 24c to move the at least one carriage 24a and/or 24b.

To guarantee the correct movement of the at least one carriage 24a and/or 24b, the slider 25b is suitable to implement at least one from among: a radial constraint suitable to prevent sliding of the at least one carriage 24a and/or 24b in a direction perpendicular to the central axis 2c with respect to the slider 25b; and an axial constraint suitable to prevent sliding of the at least one carriage 24a and/or 24b in a direction parallel to the central axis 2c with respect to the slider 25b. Preferably, the slider 25b is suitable to implement both a radial constraint and an axial constraint.

The radial constraint is achieved by means of two engagement surfaces 24c on each carriage 24a and 24b obtained on surfaces of the support 241 substantially parallel to the circular trajectory of extension 2b and opposite one another; and by means of engagement means 251 and, in particular, the movement wheels arranged in two rows with the carriage between them. In detail, the engagement means 251 and, in particular, the movement wheels are arranged along a first row/trajectory substantially concentric ad proximal to the central axis 2c and in a second row/trajectory substantially concentric and distal to the central axis 2c and having a radius different from that of the first row (FIG. 3b).

The axial constraint is achieved by means of the at least one engagement surface 24c obtained in a radial recess of the at least one carriage 24a and/or 24b so as to define, for the entire length of the carriage 24a and 24b, two abutments that are substantially transversal and, in particular, substantially perpendicular to the central axis 2c and suitable to enclose between them the engagement means 251 to prevent any axial sliding of the carriage.

The slider 25b may be integral with the curved base module 231. Alternatively, the slider 25b is movable with respect to the curved base module 231 (FIG. 6) and may comprise a support 252 for the engagement means 251; and driving means 253 comprising, preferably, one or more driving wheels suitable to push the slider 25b and, thus, the at least one carriage 24a and/or 24b along the circular trajectory of extension 2b.

The support 252 has a main trajectory of extension that practically coincides with the circular trajectory of extension 2b. Preferably, the support 252 and the slider 25b have an angular amplitude that is practically less than 20°, in detail, less than 10° and, more in detail, practically comprised between 8° and 5°. The support 252 is defined by a plate suitable to be arranged substantially perpendicular to the central axis 2c and extending along the circular trajectory of extension 2b. More preferably, it is practically parallel and, in detail, proximal to a lateral base plate 2313.

The driving wheels may be toothed so as to engage with a rack obtained in the curved base module 231; or, alternatively, a friction wheel, that is a wheel suitable to engage with a smooth surface of the curved base module 231 and to exploit the friction force between the wheel and said smooth surface to move the slider 25b.

In the case of a movable slider 25b, the radial constraint, between the slider 25b and the curved base module 231 can be obtained by arranging the driving wheels, that is the driving means 253, on opposite sides of the support 252 so that they come into contact with and slide along opposite surfaces of the curved base module 231. The axial constraint, between the slider 25b and the curved base module 231 can be obtained by arranging the driving wheels and making them slide in a channel obtained in the curved base module 231 and defining the aforesaid two abutments that are substantially transversal and, in particular, substantially perpendicular to the central axis 2c and suitable to enclose between them the driving means 253 to prevent any axial sliding of the carriage.

Lastly, the number of sliders 25b in the gantry 2 is preferably at least equal to the angular amplitude of the curved base module 231 divided by the angular amplitude of the at least one carriage 24a and/or 24b. Note that, in some cases, the engagement means 251 are suitable to integrally connect the at least one carriage 24a and/or 24b to the support 252 and, thus, the motion of the carriages 24a and 24b, when placed in the curved base module 231, is obtained thanks to the driving means 253 which, by moving the sliders 25b, pull the support carriages 24a and 24b along the circular trajectory of extension 2b.

To improve the positioning of the at least one carriage 24a or 24b on a slider 25b, one slider 25b may comprise reference means 254 (FIG. 6) suitable to refer the carriage 24a or 24b to the slider 25b along at least one reference axis chosen between an axis substantially radial to the central axis 2c and one practically parallel to said central axis 2c. In some cases the reference means 254 refer the at least one carriage 24a or 24b to the slider 25b along a first reference axis substantially radial to the central axis 2c and a second reference axis practically parallel to the central axis 2c. The reference means 254 comprise, for each reference axis, at least one reference tooth 2541 integral with the slider 25b and extending practically perpendicularly to the reference axis; and at least one sliding slot 241a, appropriately a through slot, obtained in each carriage 24a or 24b and inside which the reference tooth 2541 slides to guarantee the correct positioning of the carriage 24a or 24b with respect to the slider 25b.

Lastly, each slider 25b may comprise a coupling, suitable to appropriately integrally connect the slider 25b to a curved mobile module 232a and 232b which can therefore be moved by the slider 25b along the circular trajectory of extension 2b relative to the curved base module 231.

In the case of a passive base guideway 25, it may comprise at least a base rail system 25c (FIGS. 7a-8b) integral with and inside the curved base module 231. The base rail system 25c has an angular amplitude practically not greater than and, in detail, practically equal to the angular amplitude of the curved base module 231 so as not to protrude from the latter. Preferably, the base rail system 25c has an angular extension that is substantially practically less than 240° and, more in detail, substantially less than 210° and, yet more in detail, substantially comprised between 190° and 180°. Preferably the gantry 2 comprises a single base rail system 25c integral with the curved base module 231 on the inside face of one of the distal base plate 2312 and the lateral plates 2313. More preferably, it is integral with the inside face of the distal base plate 2312. Here and in the rest of this document, the term inside face refers to a surface facing the housing volume defined by the casing 23.

The base rail system 25c may comprise a base guiding surface 255 for the carriage 24a and/or 24b. The base guiding surface 255 may be provided with engagement teeth or be smooth. In some cases, the base rail system 25c (FIG. 8b) may comprise a base member 256 defining the base guiding surface 255 and a base spacer 257 suitable to keep the base member 256 and, thus, the base guiding surface 255, at a distance from the curved base module 231 by defining a guideway with a biconnected cross section, preferably a monoconnected cross section, and more preferably, a T-shaped cross section. Preferably, the base spacer 257 is suitable to allow the base member 256 to protrude inside at least one of the curved mobile modules 232a and 232b so that the base guiding surface 255 is arranged inside said curved mobile modules 232a and 232b. As a consequence each curved mobile module 232a and/or 232b comprises, for each base rail system 25c, an opening 2324 (FIG. 8a) in which the base guideway 25 is housed and slides; and optionally, a cover of the opening 2324.

The opening 2324 is obtained in the plate of the mobile module 232a and 232b substantially adjacent to that for connecting the base guideway 25c to the curved base module 231. The cover is suitable to cover the portion of the opening 2324 outside the base casing 231 and which would, therefore, be visible. It is integral with the mobile module 232a and/or 232b and comprises a gasket, in the form of a polymer sheet, suitable to cover the opening 2324 and a gasket retractor. The gasket may also be a metallic strip wound in a coil.

The gasket has one end integral with the curved base module 231 and one integral with the retractor; the retractor is integral with a curved mobile module 232a or 232b. Therefore, during the transition to a working configuration the gasket extends to cover the visible portion of the opening 2324; whereas during the transition to the rest configuration the retractor retracts the gasket and winds it up.

In the case of a base guideway 25 comprising at least one base rail system 25c the at least one carriage 24a and/or 24b may comprise at least one sliding member 243 on the base guiding surface 255. In particular, it comprises two sliding members 243 spaced apart along the circular trajectory of extension 2b so as to engage with the base guiding surface 255 at separate points. More in particular, the at least one carriage 24a and 24b comprises a sliding member 243 proximal to the tail end of the support 241 (that is of the carriage 24a and 24b) and a sliding member 243 proximal to the head end of the support 241 (that is of the carriage 24a and 24b). The two sliding members 243 have a reciprocal angular distance of at least 10° and, precisely, 20°. If the base guideway 25 is suitable to move the at least one mobile module 232a and/or 232b it may comprise an additional sliding member 243 identical to the sliding member 243 described below.

Each sliding member 243 (FIG. 8b) comprises a wheel 2431 for engaging with the base guiding surface 255 hinged to the support 241; and, appropriately, anti-detachment means suitable to guarantee the engagement of the wheel 2431 with the base guideway 25. The wheel 2431 may comprise, in the case of a toothed base guiding surface 255, a toothed wheel or, on the case of a smooth base guiding surface 255, a friction wheel, that is suitable to exploit the friction force to move the at least one carriage 24a and/or 24b. Preferably, the wheel 2431 is motorised. The anti-detachment means are suitable to allow the at least one carriage 24a and/or 24b to move exclusively along the base sliding trajectory 25a.

They therefore define a radial constraint of the at least one carriage 24a and 24b, that is a constraint to prevent any movement of the at least one carriage 24a and 24b in a direction substantially radial to the circular trajectory of extension 2b; and/or an axial constraint of the at least one carriage 24a and 24b, that is a constraint to prevent any movement of the at least one carriage 24a and 24b along the central axis 2c. Preferably, the anti-detachment means are suitable to implement said axial constraint and said radial constraint.

To obtain the radial constraint, the anti-detachment means comprise at least one contrast roller 2432 hinged, appropriately idly, to the support 241 to define an axis of rotation substantially parallel to that of the wheel 2431 and suitable to come into contact with the base member 256 on the side opposite the wheel 2431. In detail, the contrast roller 2432 is suitable to slide along a contrast surface of the base member 256 parallel to and opposite the base surface 25b. Preferably, the anti-detachment means comprise two contrast rollers 2432 suitable to slide along the contrast surface on opposite sides with respect to the base spacer 257.

To obtain the axial constraint, the anti-detachment means comprise at least one side plate 2433 suitable to come into contact with a surface of the base member 256 practically perpendicular to the central axis 2c to prevent any motion of the carriage 24a and 24b along the central axis 2c. Preferably, the anti-detachment means comprise two side plates 2433 suitable to enclose between them the base member 256. The ends of the side plates 2433 may be tapered along the base sliding trajectory 25a so as to facilitate the insertion of the base guideway 25 between said side plates 2433.

In some cases, the base rail system 25c and the base guiding surface 255 are defined by an inside face of the curved base module 231, in particular, by an inside face chosen from between the distal base plate 2312, the side plates 2313 and, more in particular, by the inside face of the distal base plate 2312 of the curved base module 231. In this case, the sliding member 243 may comprise return means suitable to rest the wheel 2431 against or move it away from said inside face of the curved base module 231 when the carriage is in the curved base module 231. In that case the curved mobile modules 232a and 232b may be without the mobile plates 2321 and 2322.

The mobile guideway 26 is integral with and inside the at least one curved mobile module 232a and/or 232b. It therefore has an angular extension that is practically equal to the total angular extension of the at least one curved mobile module 232a and 232b. It has an extension that is substantially practically less than 240° and, preferably, substantially less than 210° and, more preferably, substantially comprised between 190° and 180°.

In order to allow the curved mobile modules 232a and 232b to move independently of one another, the mobile guideway 26 may be divided into sections each of which is integral with a curved mobile module. It is important to note that having a mobile guideway 26 divided into several sections, it is possible to define, in addition to the areas of superimposition on the base guideway 25 and in the case of mobile modules that can be inserted into one another, additional areas of superimposition of one sector of a curved mobile module over one sector of a separate curved mobile module.

In detail, the mobile guideway 26 comprises a first sector 26b integral with the first curved mobile module 232a and suitable to move the at least one carriage 24a and/or 24b along the mobile sliding trajectory 26a when it is in the first curved mobile module 232a; and a second sector 26c integral with the second curved mobile module 232b and suitable to move the at least one carriage 24a and/or 24b along the mobile sliding trajectory 26a when it is in the second curved mobile module 232b. The presence of the two sectors 26b and 26c makes it possible to define two areas of superimposition, that is a first area of superimposition 26d of the first sector 26*b* over the base guideway 25 and a second area of superimposition 26*e* of the second sector 26*c* over the base guideway 25, see FIGS. 7*b* and 4*e*. Each sector 26*b* and 26*c* has an angular amplitude that is substantially not more than and, preferably, practically equal to the angular amplitude of the curved mobile module 232*a* and 232*b*. In particular, it has an angular extension that is practically less than 140°, more in particular, practically less than 120° and, yet more in particular, substantially comprised between 100° and 85°.

The mobile guideway 26 and, thus, the sectors 26*b* and 26*c*, may be active, that is appropriately motorised so as to control the sliding of the carriage 24*a* and/or 24*b* along the mobile sliding trajectory 26*a*, or alternatively passive and, thus, it is at least one carriage 24*a* and/or 24*b* that is motorised. Note that the guideways 25 and 26 may both be active, or the guideways 25 and 26 may both be passive, or one of the guideways 25 and 26 may be active and the other passive.

In the case of the mobile guideway 26 being active, the guideway 26 and, in particular, each sector 26*b* and 26*c* may comprise one or more thrust members 261 (FIGS. 4*a*-4*e*), at least partly appropriately electrically motorised, suitable to engage with at least one engagement surface 24*c* and, thus, to generate the thrust force to move the at least one carriage 24*a* or 24*b* along the circular trajectory of extension 2*b*. The thrust members 261 are defined by wheels, spheres or other similar elements arranged along a substantially circular trajectory practically centred on the central axis 2*c* so as to allow the at least one carriage 24*a* or 24*b* to move along the mobile sliding trajectory 26*a*. The thrust members 261 are defined by toothed wheels suitable to engage with an engagement surface 24*c* provided with teeth, or a friction wheel, that is a wheel suitable to engage with a smooth engagement surface 24*c* and to exploit the friction force between the wheel and said smooth engagement surface 24*c* to move the at least one carriage 24*a* and/or 24*b*.

To guarantee the correct engagement of the at least one carriage 24*a* and/or 24*b* with the mobile guideway 26, the mobile guideway 26 defines at least one from among: an axial constraint suitable to prevent sliding of the at least one carriage 24*a* and/or 24*b* parallel to the central axis 2*c* with respect to said mobile guideway 26; and a radial constraint suitable to prevent sliding, perpendicular to the central axis 2*c*, of the at least one carriage 24*a* and/or 24*b* with respect to the mobile guideway 26. Appropriately, the mobile guideway 26 defines both an axial constraint and a radial constraint. The axial constraint between the mobile guideway 26 and the carriage 24*a* and/or 24*b* is appropriately implemented in the same way as that between the base guideway 25 and the carriage 24*a* and/or 24*b*.

It is therefore obtained by means of the at least one engagement surface 24*c* obtained in a radial recess of the at least one carriage 24*a* and/or 24*b* so as to define, for the entire length of the at least one carriage 24*a* and 24*b*, two abutments that are substantially transversal and, in particular, substantially perpendicular to the central axis 2*c* and suitable to enclose between them the thrust means 261 to prevent any axial sliding of the carriage with respect to the mobile guideway 26.

To define the radial constraint, the mobile guideway 26 may envisage the thrust means 261 arranged practically in separate rows, one concentric and proximal to the central axis 2*c* and one concentric, distal from the central axis 2*c* and with a different radius from the first row (FIG. 4*b*) so as to enclose between them the at least one carriage 24*a* and/or 24*b* and prevent any radial sliding. In the case of a passive mobile guideway 26, the mobile guideway 26 and, thus, each sector 26*b* and 26*c*, may comprise at least one mobile rail system 262 defining a mobile guiding surface 262*a* (FIGS. 7*a*-8*b*) for the carriage 24*a* and/or 24*b*.

The mobile guiding surface 262*a* may be provided with engagement teeth or alternatively it may be smooth. Preferably, the mobile guideway 26 and, thus, each sector 26*b* and 26*c*, comprises two mobile rail systems 262 defining mobile guiding surfaces 262*a* having different radii. A mobile rail system 262 may comprise a mobile member 2621 integral with the curved mobile module 232*a* and/or 232*b* and defining said mobile guiding surface 262; and, in some cases, a spacer 2622 suitable to keep the mobile member 2621 and, thus, the mobile guiding surface 262*a*, at a distance from the curved mobile modules 232*a* and 232*b* by defining a mobile guideway 26 with a biconnected cross section, preferably a monoconnected cross section, and more preferably, a T-shaped cross section.

Alternatively, the mobile guiding surface 262*a* may be defined by an inside face of the mobile modules 232*a* and 232*b*, in particular, by an inside face chosen from among those of the distal mobile plate 2322 and the lateral mobile plates 2323 and, more in particular, by the inside face of the lateral mobile plates 2323 of the curved mobile modules 232*a* and 232*b*.

In order to slide on the mobile guiding surface 262*a* the carriage 24*a* and/or 24*b* may comprise at least one handling assembly 244 (FIG. 8*b*) suitable to control the movement of the at least one carriage 24*a* and/or 24*b* along said mobile guiding surface 262*a*. In particular, the at least one carriage 24*a* and/or 24*b* may comprise two handling assemblies 244 arranged at a distance from one another along the trajectory of extension 2*b* so as to engage with the mobile guideway 26 at different points. More in particular, it may comprise a handling assembly 244 proximal to the tail end of the carriage 24*a* and/or 24*b* and a handling assembly 244 proximal to the head end. The two handling assemblies 244 have a reciprocal angular distance of at least 10° and, in detail, 20°.

Alternatively, the two handling assemblies 244 are arranged on opposite sides of the support 241 so as to engage with the mobile circulation system 26 arranged on opposite plates of the first curved mobile module 232*a* and of the second curved mobile module 232*b*.

According to a further alternative embodiment, the at least one carriage 24*a* and/or 24*b* comprises two pairs of handling assemblies 244. Said pairs are arranged at an appropriate distance from one another along the circular trajectory of extension 2*b* so as to engage with the mobile guideway 26 at different points and, in particular, one is arranged at the head end and one at the tail end of the carriage 24*a* and/or 24*b*. One handling assembly 244 comprises at least one rolling member 2441 hinged to the support 241 and suitable to engage with the mobile guiding surface 262*a*; and, appropriately, anchor means suitable to guarantee the correct engagement of the rolling member 2441 with the mobile guideway 26. The rolling member 2441 may be a toothed wheel, in the case of a toothed guiding surface 262*a*, or a friction wheel in the case of a smooth mobile guiding surface 262*a*. Preferably, the rolling member 2441 is motorised.

The anchor means are suitable to allow the carriage 24*a* and/or 24*b* to move exclusively along the mobile sliding trajectory 26*a*. They therefore define the radial and/or axial anchoring of the at least one carriage 24*a* and/or 24*b*.

To obtain radial anchoring, the anchor means comprise at least one central plate 2442 attached to the support and suitable to come into contact with a surface of the mobile members 2621 substantially parallel to the central axis 2c. In particular, the anchor means comprise a single central plate 2442 suitable to be placed between and come into contact with a connected pair of mobile members 2621 engaged with a same plate of a curved mobile module 232a and 232b.

The ends of the central plate 2442 may be tapered along the mobile sliding trajectory 26a so as to facilitate its insertion between the mobile members 2621. To obtain axial anchoring, the anchor means comprise at least one contrast roller appropriately idly hinged to the support 241 to define an axis of rotation that is practically parallel to that of the rolling member 2441 and suitable to come into contact with a mobile member 2621 on the side opposite the rolling member 2441. In detail, the contrast roller is suitable to slide along a contrast surface of the mobile member 2621 and, more in detail, substantially parallel to and opposite the mobile guiding surface 26. Note that in the case of second mobile members 2621, the additional contrast roller may be omitted as the axial constraint is defined by the two second wheels of the two handling assemblies 244 coming into contact with the base guideways 25 on inside faces of opposite lateral mobile plates 2323.

Lastly, the at least one carriage 24a and/or 24b may comprise at least one brake 245 suitable to integrally connect said carriage 24a and/or 24b to at least one of the curved modules 231, 232a and 232b. In detail, the brake 245, according to a command sent from the control unit 1a, is able to integrally connect the carriage 24a and/or 24b to a single module (to the curved base module 231, to the first curved mobile module 232a or to the second curved mobile module 232b) or to a pair of modules (curved base module 231 and first curved mobile module 232a, curved base module 231 and second curved mobile module 232b, or first curved mobile module 232a and second curved mobile module 232b).

A brake 245 may comprise at least one linear actuator integral with the at least one carriage 24a and/or 24b defining a high-friction pressure surface with an curved module 231, 232a and 232b. Said linear actuator is suitable to vary its length, appropriately along an axis practically radial with respect to the circular trajectory of extension 2b, so as to press the pressure surface against one of the curved modules 231, 232a and 232b and integrally attach the carriage 24a and/or 24b to the curved modules 231, 232a e 232b or, otherwise, to move the pressure surface away from the curved modules 231, 232a e 232b and allow a movement of the at least one carriage 24a and/or 24b with respect to said curved modules 231, 232a e 232b.

For the sake of completeness, note that, in some cases, the guideways 25 and/or 26 may be arranged on the proximal plates 2321 and 2311, respectively. In this case the base guideway 25 and/or the mobile guideway 26 are made of a material that is transparent to X-rays, and preferably with a radiodensity of, on average, substantially less than 400 HU (Hounsfield units), more preferably, less than 100 HU. They are preferably made of a composite material with a polymeric matrix. For example, the polymeric matrix is resin and more preferably an epoxy resin or similar material, whereas the reinforcement is preferably made of fibre, yet more in detail, of carbon fibre or aramid or glass fibre.

The control unit 1a is connected to the other components of the device 1 by means of a cable 1b and/or via wireless connection. It is suitable to control and operate at least the gantry 2 and its movements. The unit 1a comprises a control board suitable to automatically control and actuate the imaging device 1; and interface components (touch-screen, keyboard, etc.) suitable to allow the operator to control the imaging device 1.

In particular, the control unit 1a is suitable to control the operation of the at least one retainer and, to be precise, the transition from a locked position to a released position. More in particular, when the control unit 1a sets the retainers to the locked position, it locks the gantry 2 in the desired configuration and the carriage 24a and/or 24b slides in the housing volume and moves the unit being transported (source 22 and/or detector 21) and, when it sets at least one of the retainers to the released position, it permits the carriage 24a and/or 24b to perform a relative movement between at least one mobile module 232a and 232b with respect to the curved base module 231 and, thus, a change in the configuration of the gantry 2.

In addition to the gantry 2 and the unit 1a, the imaging device 1 may comprise a load-bearing structure 3 suitable to support and move the gantry 2 and defining a free chamber 3a for the gantry 2; and, in some cases, a bed 4 suitable to be at least partially inserted in the analysis zone 2a and defining a longitudinal axis 4a and a surface 4b to support the patient. The support surface 4b is substantially parallel to the central axis 2c and is suitable to be arranged practically parallel to the surface supporting the imaging device 1. The load-bearing structure 3 comprises a base 31 suitable to support the gantry 2; at least one column 32 suitable to hold the bed 4 in a raised position relative to the base 31; and, in some cases, actuators 33 suitable to move the bed 4 with respect to the base 31.

Optionally, the imaging device may be of the transportable type and, thus, the load-bearing structure 3 may comprise movement means 34 for moving the device 1, preferably pivoting wheels, suitable to be arranged between the floor and the base 31 to permit the movement of the device 1. The base 31 and the at least one column 32 delimit the free chamber 3a. In detail, the free chamber 3a is delimited at the bottom, i.e. close to the floor, by the base 31; along one side face by the column 32; if present, along a second side face opposite the first by the second column 32; and, optionally, at the top by the bed 4. The free chamber 3a therefore has two open sections giving access to said chamber extending substantially parallel to the central axis 2c and, in particular, practically perpendicular to the support surface 4b.

The actuators 33 are arranged between the bed 4 and each column 32 so as to modify the extension of the free chamber 3a through a translational movement practically transversal and, in particular, perpendicular to the support surface 4b or, alternatively, to work independently to tilt the support surface 4b relative to the axis of the gantry. Alternatively, the actuators 33 modify the free chamber 3a by rotating the bed 4 about an axis substantially parallel to the central axis 20a.

Arranged between the base 31 and the gantry 2 of the imaging device 1 there are means of rotation 5 which define an axis of rotation 5a of the gantry 2; and means of translation 6 which define an axis of translation 6a of the gantry 2. The means of translation 6 are arranged between the base 31 and the gantry 2 and comprise a linear guideway 61, preferably motorised, suitable to control the translation along the axis of translation 6a; a translation element 62 connected to the gantry 2 and, in particular, to the curved base module 231 and suitable to slide along the linear guideway 61 thus translating said gantry 2. The axis of translation 6a is substantially parallel to the central axis 2c.

The means of rotation 5 are arranged between the means of translation 6 and the gantry 2 and are suitable to rotate the gantry 2 with respect to an axis of rotation 5a substantially transversal to the central axis 2c and, appropriately, to the support surface 4b so as to alter the reciprocal angle of inclination between the axes 2c and 4a. The means of rotation 5 comprise a fixed plate 51 suitable to be connected to the translation element 62; a mobile plate 52 connected to the casing 23 and, precisely, to the curved base module 231; pins, bearings or other similar elements defining the axis of rotation 5a; and a control lever 53 suitable to be held by the operator and, thus, to permit said operator to manually control the rotation, about the axis of rotation 5a, of the mobile plate 52 and, thus, of the gantry 2 with respect to the fixed plate 51.

The control lever 53 is suitable to be connected to holes provided in the plates 51 and 52 so as to define, for the gantry 2, a first rotational locked position in which the central axis 2c is substantially parallel to the longitudinal axis 4a, the circular trajectory of extension 2b lies in a plane that is substantially perpendicular to the longitudinal axis 4a; and a second rotational locked position in which the central axis 2c is practically perpendicular to the longitudinal axis 4a, the trajectory of extension 2b lies in a plane that is practically parallel to the longitudinal axis 4a. Additionally, the control lever 53 defines a third rotational locked position in which the central axis 2c is substantially parallel to the longitudinal axis 4a, the trajectory of extension 2b lies in a plane that is practically perpendicular to the longitudinal axis 4a but the gantry 2 is rotated by 180° with respect to the first position.

Instead of the lever 53, the means of rotation 5 consist of a motor suitable to control the aforesaid rotation of the gantry 2 and to define the first and the second rotational locked position and, if present, the third position.

Lastly, the imaging device 1 comprises one or more cover assemblies 7, preferably two, suitable to seal the ends of the casing 23 and, in particular, of the curved mobile modules 232a and 232b when the device 1 is at least in the closed configuration and, preferably, in any of the working configurations except in the fully extended configurations. Each cover assembly 7 comprises at least a protection 71, one for each end of the curved mobile modules 232a and 232b suitable to come out of the curved base module 231, defined by a plate, a slat system or other similar element detachably connected to said end of one of the curved mobile modules 232a and 232b in order to close said end.

Preferably, the motion of the protection 71 may be passive, that is obtained by means of springs or the like, or active and, thus, controlled by a motor, not illustrated in the figure, suitable to move the protection 71 relative to said ends. Appropriately, said motor moves the protection 71 by means of a rotation relative to an axis substantially parallel to the central axis 2c. In particular, the motor is suitable to place the protection 71 over the ends of the casing 23 to close the gantry 2 when the device is in the rest configuration or in a working configuration in which it is not fully extended; and to move the protection 71 away from the end of the gantry 2 to enable the correct expansion of the gantry 2 when the device 1 is in the fully extended working configuration and allow the carriage 24a and/or 24b to pass from one curved mobile module 232a and/or 232b to the other.

Figure 1D:
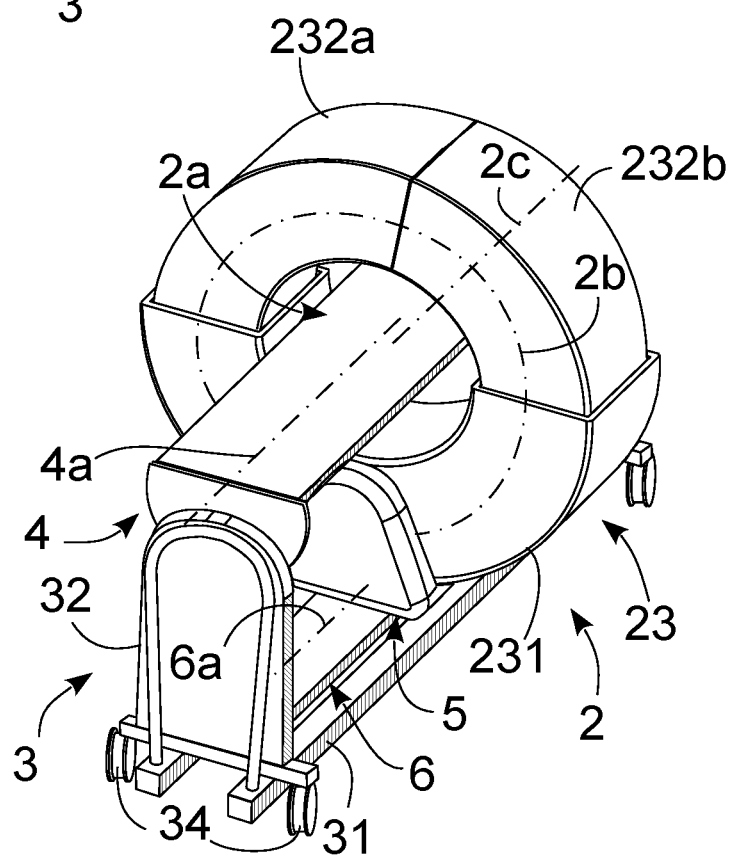
FIG. 1d illustrates the imaging device in a configuration subsequent to that shown in FIG. 1b.
Figure 4A:
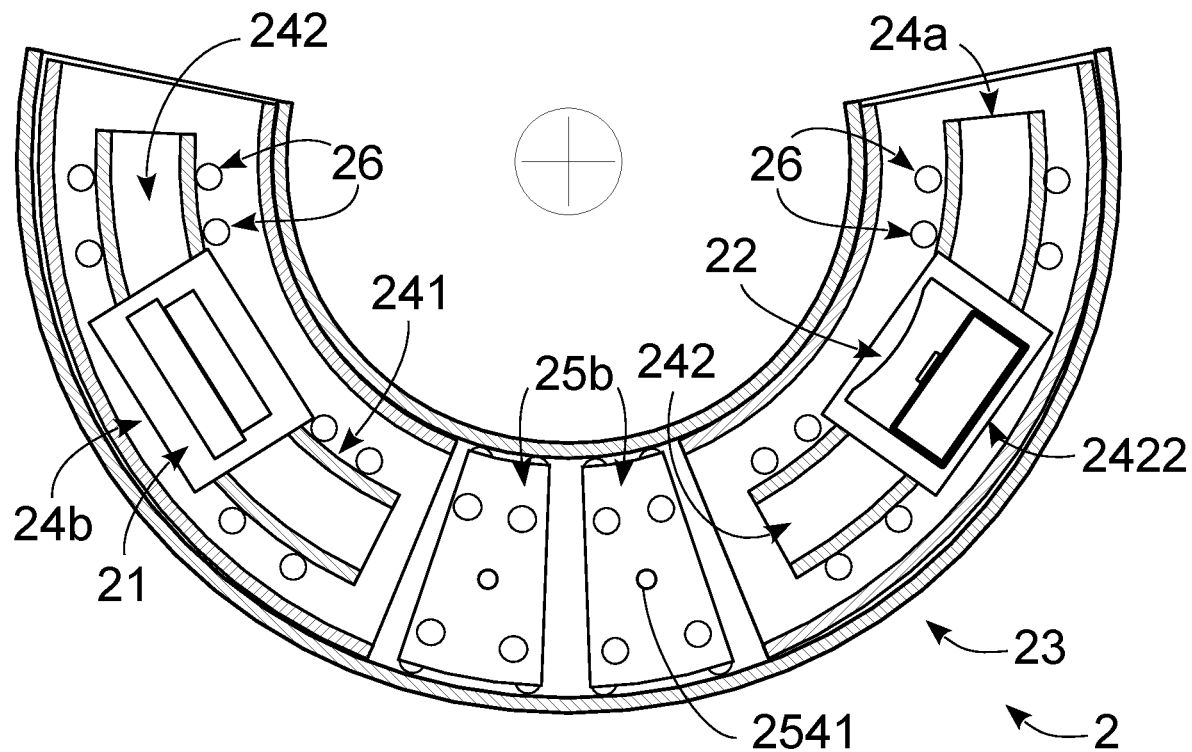

The functioning of an imaging device described above in a structural sense, is as follows. Initially, the imaging device 1 is in the rest configuration, that is, with the gantry 2 arranged inside the free chamber 3a and, thus, the support surface 4b practically completely free and substantially accessible from any point. In this rest configuration the gantry 2 has the casing 23 with the curved mobile modules 232a and 232b, the carriages 24a and 24b, the source 22 and the detector 21 housed inside the curved base module 231. The operator places the patient on the bed 4 and controls the transition to a desired working configuration (FIGS. 1c, 1d).

In particular, the control unit 1a activates the means of rotation 5 to rotate the gantry 2 by approximately 90° so that the axes 2c and 4a are substantially parallel to one another. In this step, the casing 23 and the gantry 2 adjust their extension along the circular trajectory of extension 2b until reaching the desired angular extension. If the gantry 2 becomes substantially closed and, thus, has an extension of approximately 360° (fully extended working configuration), each protection 71 is moved away from the ends of the curved mobile modules 232a and 232b to free said ends. During this change of configuration the curved mobile modules 232a and 232b rotate, along the circular trajectory of extension 2b, in opposite directions so that said curved mobile modules 232a and 232b and the sectors 26b and 26c are arranged on opposite sides in relation to the central axis 2c and, in the fully extended working configuration, they substantially come into contact with one another. The motion of the first curved mobile module and of the second curved mobile module 232b is respectively defined by the carriages 24a and/or 24b.

In detail, to change the configuration of the gantry 2, each carriage is placed in one of the areas of superimposition 26d and/or 26e, is coupled to a curved mobile module 232a or 232b by means of the brake 245 and presses on the curved base module 231 to make the curved mobile module 232a or 232b to which it is anchored move relative to the curved base module 231. When the gantry 2 has reached the desired configuration, the control unit 1a moves the retainers to the locked position so as to integrally couple the modules 231, 232a and 232b and, thus, lock the gantry 2 in the desired working configuration, such as the fully extended configuration. At the same time, the brake 245 releases the coupling between the carriage 24a and 24b and the curved mobile module 232a or 232b so that the carriage 24a and 24b is able to move freely. Note that the relative motion between the curved modules 231, 232a and 232b moves the cover, if present. In detail, owing to said relative motion, the polymer sheet extends and covers the opening portion 2324 revealed when the curved mobile modules 232a and 232b come out of the curved base module 231, in order to prevent any dirt or other material from entering the housing volume.

At this point, the operator selects the part of the body to be examined and, as a consequence, the control unit 1a orders one or more of the carriages 24a and 24b to slide along the guideways 25 and 26 and place the image acquisition unit in the desired position. During said movement, one carriage 24a and/or 24b, as it moves from the curved base module 231 to the first curved mobile module 232a, disengages from the base guideway 25 and engages with the mobile guideway 26 as it stops sliding along the base sliding trajectory 25a and starts sliding along the first mobile sliding trajectory 26a. Furthermore, during said transition, the carriage 24a and/or 24b engages with the base guideway 25 and with the mobile guideway 26. When the gantry 2 reaches the desired position, automatically or in response to a command sent by the operator using the control unit 1a, image acquisition is performed.

When the imaging procedure is complete, the operator may perform another imaging procedure or control the return of the device 1 to the rest configuration and then perform surgery on the patient without ever moving the patient from the bed 4 of the device. The functioning described above achieves an innovative procedure for activating a deactivating an imaging device that can be implemented by the imaging device described above in a structural and functional sense.

The activation and deactivation procedure comprises an opening step in which the carriage 24a and/or 24b moves the curved mobile module 232a or 232b relative to the curved base module 231 and the gantry 2 moves from the rest configuration to a working configuration; and a closing step, appropriately after performing a radiological image acquisition procedure, in which the carriage 24a and/or 24b moves the curved mobile module 232a or 232b relative to the curved base module 231 in the opposite direction to the previous step and the gantry 2 moves from the working configuration to a rest configuration.

The opening step comprises a positioning sub-step in which the carriage 24a and/or 24b is at least partially in one of the mobile modules 232a, 232b and partially in the curved base module 231; a connection sub-step in which the carriage 24a and/or 24b is integrally connected to just one of the curved mobile modules 232a and 232b; a movement sub-step in which the carriage 24a and/or 24b moves the curved mobile module 232a, 232b relative to and by applying force on the curved base module 231; and a releasing sub-step in which the carriage 24a and/or 24b releases the curved mobile module 232a or 232b.

In the positioning sub-step, as described in more detail above, a carriage 24a and/or 24b is placed in the area of superimposition 26d and/or 26e of the curved mobile module 232a or 232b to be moved. In the connection sub-step the brake 245 integrally couples the carriage 24a and/or 24b to the curved mobile module 232a or 232b and blocks, for example, the rotation of the rolling members 2441. In the subsequent movement sub-step the carriage 24a and/or 24b, thanks to the aforesaid restraint, pushes the curved base module 231 which, since it is integral with the rest of the device, remains stationary. As a consequence, said thrust is transferred to the carriage 24a and/or 24b and, thanks to the integral coupling implemented by means of the brake 245, to the mobile module 232a or 232b which thus moves along the circular trajectory of extension 2b.

When the gantry 2 has reached the desired configuration the movement sub-step ends and the release sub-step begins. In this release sub-step the brake 245 releases the coupling between the carriage 24a and/or 24b and the curved mobile module 232a or 232b so that the carriage 24a and/or 24b is able to move freely. At the same time, the retainer moves to the lock position to integrally connect the modules 231, 232a and 232b and thus lock the gantry in the desired working configuration, for example in the fully extended configuration.

The closing step comprises a sub-step of positioning the carriage 24a and/or 24b; a sub-step of connecting the carriage 24a and/or 24b to the curved mobile module 232a or 232b to be moved; a sub-step of moving the curved mobile module 232a or 232b; and a releasing sub-step in which the carriage 24a and/or 24b releases the curved mobile module 232a or 232b. The sub-steps are substantially the same sub-steps as those in the opening step. Therefore, for their description reference should be made to the corresponding sub-steps of the opening step.

The disclosed embodiments achieve some important advantages. One of the most important advantages lies in the fact that, because it is possible to vary the extension of the gantry 2 and, thus, place it under the bed 4, the imaging device 1 can be used to perform a plurality of operations/analyses (SPECT, CT or PET) on the patient without having to remove the patient from the bed 4, even for long periods of time, but without undermining the possibility of performing scans at any angle.

Therefore, the innovative device allows the operator to leave the patient on the bed all the time and to perform both surgical procedures and radiological scans of different types (X-rays, tomography and fluoroscopy) from absolutely any angle.

The innovative telescopic casing 23, along with the guideways 25 and 26, allow the operator to arrange the gantry 2 around the patient and/or to move it away from the patient by only moving the gantry and, thus, without moving the patient. As a consequence, the device 1 becomes an instrument for continuously monitoring the patient, that is to say, it can be used at any time to perform imaging of the patient, it can be used in any hospital room (X-ray room, operating theatre, emergency unit, etc.) and, at the same time, it also allows emergency surgical operations to be performed. Furthermore, the patient can be moved from one room to another without ever leaving the device 1 according to one embodiment.

In the rest configuration, since the gantry 2 is practically entirely housed in the free chamber 3a, the overall dimensions of the device 1 are defined exclusively by the bed 4 and by the load-bearing structure 3. They are therefore substantially equal to those of an examination couch, that is, a bed of the type normally used to transport patients within the hospital or on which surgery is performed and the device 1 is therefore able to pass through doors, enter lifts or pass through other openings normally present in a hospital. This feature is further enhanced by the fact that, thanks to the innovative gantry 2, the imaging device 1 does not have to be placed in a shielded room and/or rooms provided with the specific conditions that characterise the radiology rooms currently in use.

Another advantage is that since the guideways 25 and 26 define a path of rotation of the source and of the detector with an angular amplitude of 360°, scans can be performed at 360° or more without any interruption. Since the carriage 24a and/or 24b is able to move without distinction on the guideways 25 and 26, it is able to make the image acquisition unit rotate at any angle.

Another advantage is given by the fact that the imaging device 1 has an extremely simple structure, thanks to the possibility of using the carriages 24a and/or 24b to move the image acquisition unit and to vary the configuration of the gantry 2.

A no less important advantage is due to the presence of the cover assemblies 7 which, by sealing the ends of the gantry 2 when the device 1 is in the rest configuration, prevent the entry of any blood, debris or other material which could damage the internal components of the gantry 2. This advantage is enhanced by the presence of the cover which, by sealing the opening 2324, prevents dirt or other elements that could undermine operation from entering the housing volume.

An important advantage lies in the fact that, during image acquisition, the casing 23 remains substantially stationary in that the movement of the image acquisition unit is performed by components inside said casing. The immobility of the casing 23 during scanning prevents the risk of any moving parts colliding with and injuring the patient.

Another feature of the immobility of the casing 23 is that scanning can be performed without an operator. Because the operator does not have to prevent mobile parts of the gantry 2 from colliding with the patient, he or she can move away from the so-called patient area and, thus, from the source 22. As a consequence, the operator is not unnecessarily exposed to harmful ionising radiation.

In addition, because the operator is far away, said operator does not obstruct the visibility of any navigation/viewing systems on the gantry 2 or on the imaging device 1. Moreover, any catheters, ECG and/or EEG wires, or other medical devices that may be connected to the patient do not obstruct moving mechanical parts of the gantry 2 during the scan.

Another advantage lies in the fact that thanks to the actuators 33 that can be operated separately, the bed 4 has two degrees of freedom with respect to the structure 3 and the gantry 2. It can in fact be moved along an axis that is substantially perpendicular to the support surface 4b and can be tilted/rotated with respect to the central axis 2c.

A further advantage consists of the fact that the plates 2312 and 2322 are free, that is, there are no elements connected to them which could interfere with the image acquisition.

Modifications and variations may be made to the embodiments described herein without departing from the scope of the inventive concept as expressed in the independent and dependent claims. All details may be replaced with equivalent elements and the scope of the invention includes all other materials, shapes and dimensions.

For example, to control the reciprocal sliding of the curved modules 231, 232a and 232b, the casing 23 may comprise at least one kinematic expansion mechanism 233 suitable to move the mobile module relative to the curved base module 231 along substantially the circular trajectory of extension 2b so as to vary the angular extension of the casing 23 and, appropriately, to allow the casing 23 and, thus, the gantry 2, to stably assume any angular extension comprised between the rest configuration and the fully extended working configuration.

In particular, the kinematic expansion mechanism 233 is suitable to move the mobile modules 232a and 232b independently of one another relative to the curved base module 231 along the circular trajectory of extension 2b in opposite directions so that, in the fully extended working configurations, the curved mobile modules 232a and 232b come into contact with one another. The kinematic expansion mechanism 233 (FIG. 5) is of the mechanical type and, for example, comprises at least one rack 2331 practically obtained in each curved mobile module 232a and 232b and substantially extending along the circular trajectory of extension 2b; and at least one pinion 2332 hinged to the curved base module 231 so as to protrude therefrom towards the curved mobile module 232a and 232b, motorised and engaging with the racks so as to control the motion of the curved mobile module 232a and 232b along the circular trajectory of extension 2b.

Alternatively, the kinematic expansion mechanism 233 may move each mobile module 232a and 232b relative to the curved base module 231 by means of belt systems, curved actuators, for example pneumatic actuators or, according to another alternative embodiment, it may be magnetic. In order to make it possible to conceal the kinematic expansion mechanism 233 between the curved modules 231, 232a and 232b, each curved mobile module 232a and 232b is provided with a recess 2333 defining a housing channel for the kinematic mechanism.

In another example, the gantry 2 may comprise a single carriage for the image acquisition unit with a substantially curved trajectory of extension having its centre on the central axis 2c. In that case, said single carriage comprises a support 241 suitable to place the source 22 and the detector 21 on the opposite side of the central axis 2c and, thus, having an angular extension at least equal to 180° with the source 22 and the detector 21 or two detectors 21 connected at opposite ends.

Preferably, to facilitate the transition of the gantry 2 into the rest configuration, said support 241 may be of the telescopic type and, thus, suitable to vary its extension and define an extended configuration in which the source 22 and the detector 21 or the two detectors 21 are arranged on the opposite side of the central axis 2c; and a contracted configuration in which the single carriage has a shorter extension compared to the extended configuration and, thus, brings the source 22 and the detector 21 or the two detectors 21 close together.

The foregoing description of specific exemplary embodiments will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realize the different functions described herein could have a different nature without, for this reason, departing from the field of the invention, it is to be understood that the phraseology or terminology that is employed herein is for the purpose of description and not of limitation.

The invention claimed is:

1. An imaging device comprising:
    a gantry defining an analysis zone suitable to contain at least the portion of the patient to be analyzed and a circular trajectory of extension extending around a central axis;
    an image acquisition unit housed within the gantry, the image acquisition unit includes at least a detector suitable to receive an emission after the emission has traversed at least part of the analysis zone;
    a casing defining a housing volume for the at least one detector, the casing is of the telescopic type and includes a curved base module, at least one curved mobile module movable relative to the curved base module so as to vary the angular extension of the casing and, thus, of the housing volume while maintaining the image acquisition unit inside the housing volume;
    at least one carriage housed inside the housing volume to which the image acquisition unit is attached;
    a base guideway integral with the base module and defining a base sliding trajectory for the at least one carriage in the base module; and
    a mobile guideway integral with and inside the at least one curved mobile module and defining a mobile sliding trajectory for the at least one carriage in the curved mobile module.

2. The imaging device of claim 1, wherein the casing includes a first curved mobile module and a second curved mobile module, and wherein the mobile guideway includes a first sector integral with the first curved mobile module and defining a first portion of the mobile sliding trajectory) and a second sector integral with the second curved mobile module and defining a second portion of the mobile sliding trajectory.

3. The imaging device of claim 1, wherein the mobile sliding trajectory is distinct from the base sliding trajectory.

4. The imaging device of claim 1, wherein the base and mobile sliding trajectories have a different radius.

5. The imaging device of claim 4, wherein the base and mobile sliding trajectories have a different position along the central axis.

6. The imaging device of claim 1, wherein the mobile sliding trajectory is substantially distinct from the base sliding trajectory so that, when the at least one curved mobile module is moved relative to the curved base module, the base and mobile guideways slide relative to one another and are at least partially superimposed.

7. The imaging device of claim 1, wherein the at least one carriage includes at least one sliding member of the at least one carriage on the base guideway, and at least one handling assembly of the at least one carriage on the mobile guideway.

8. The imaging device of claim 1, wherein the mobile guideway includes a plurality of thrust means suitable to engage with at least one engagement surface of the at least one carriage so as to move the at least one support carriage along the mobile sliding trajectory.

9. The imaging device of claim 8, wherein the at least one engagement surface is obtained in a radial recess in the at least one carriage so as to define two abutments substantially transversal to the central axis and suitable to enclose between them the thrust means to prevent any axial sliding of the at least one carriage relative to the mobile guideway.

10. The imaging device of claim 1, wherein the base guideway includes at least a slider housed in the curved base module and suitable to move the at least one carriage along the circular base sliding trajectory.

11. The imaging device of claim 10, wherein the slider is movable relative to the curved base module.

12. The imaging device of claim 1, wherein the at least one carriage includes a support suitable to slide within the curved base model and a relative sliding module suitable to connect the acquisition unit to the support and to move the acquisition unit relative to the support.

13. A method for activating and deactivating an imaging device, the method comprising:
providing a gantry defining an analysis zone suitable to contain at least the portion of the patient to be analyzed and a circular trajectory of extension extending around a central axis, the gantry includes a casing defining a housing volume for at least one detector, the casing is of the telescopic type and includes a curved base module, at least one curved mobile module movable relative to the curved base module so as to vary the angular extension of the casing and, thus, of the housing volume while maintaining the image acquisition unit inside the housing volume, the gantry also including at least one carriage housed inside the housing volume to which the image acquisition unit is attached;
opening the gantry by moving the at least one curved mobile module with the at least one carriage relative to the curved base module;
positioning the at least one carriage partially inside the at least one curved mobile module and partially inside the curved base module, wherein the at least one carriage is integrally connected to just one of the at least one curved mobile modules;
moving the at least one curved mobile module with the at least one carriage relative to the curved base module not integral with the at least one carriage; and
closing the gantry by moving the at least one curved mobile module with the at least one carriage relative to the curved base module (231) with a trajectory having an opposite direction to that of the opening step.

* * * * *

UNITED STATES PATENT AND TRADEMARK OFFICE
CERTIFICATE OF CORRECTION

| | |
|---|---|
| PATENT NO. | : 10,925,560 B2 |
| APPLICATION NO. | : 15/771374 |
| DATED | : February 23, 2021 |
| INVENTOR(S) | : Fortuna et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 465 days.

Signed and Sealed this
Twenty-fourth Day of May, 2022

Katherine Kelly Vidal
*Director of the United States Patent and Trademark Office*